(12) United States Patent
Chien et al.

(10) Patent No.: US 8,114,581 B2
(45) Date of Patent: Feb. 14, 2012

(54) METHODS AND COMPOSITIONS FOR DETECTING NEOPLASTIC CELLS

(75) Inventors: Shu Chien, La Jolla, CA (US); Yingxiao Wang, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 160 days.

(21) Appl. No.: 11/992,031

(22) PCT Filed: Sep. 15, 2006

(86) PCT No.: PCT/US2006/036143
§ 371 (c)(1),
(2), (4) Date: Mar. 14, 2008

(87) PCT Pub. No.: WO2007/035553
PCT Pub. Date: Mar. 29, 2007

(65) Prior Publication Data
US 2009/0305309 A1    Dec. 10, 2009

Related U.S. Application Data

(60) Provisional application No. 60/717,599, filed on Sep. 15, 2005.

(51) Int. Cl.
*C12Q 1/00* (2006.01)
*C12N 15/00* (2006.01)
*C07H 21/04* (2006.01)

(52) U.S. Cl. .................. 435/4; 435/320.1; 536/23.4

(58) Field of Classification Search .................. None
See application file for complete search history.

(56) References Cited

U.S. PATENT DOCUMENTS

2002/0127676 A1    9/2002  Bonny
2003/0186229 A1*  10/2003  Tsien et al. .................. 435/6
2006/0222657 A1*  10/2006  Dowdy et al. .............. 424/186.1

OTHER PUBLICATIONS

Wang et al (Nature, Apr. 2005, 434:1040-1045, IDS).*
Wang et al (Nature, Apr. 21, 2005, 434:1040-1045, IDS).*
Wadia et al (Nature Medicine, Mar. 2004, 10:310-315, IDS).*
Wang, et al.; "Visualizing the mechanical activation of Src." Nature, Apr. 2005 vol. 434, pp. 1040-1045.
Wadia, et al. "Transducible TAT-HA fusogenic peptide enhances escape of TAT-fusion proteins after lipid raft macropinocytosis" Nature Medicine, Mar. 2004, vol. 10, No. 3, pp. 310-315.
Tsygankov, et al. "SRC: Regulation, Role in Human Carcinogenesis and Pharmacological Inhibitors" Current Pharmaceutical Design, Jun. 15, 2004, vol. 10, No. 15, pp. 1745-1756 (Abstract only).

* cited by examiner

*Primary Examiner* — Laura B Goddard
(74) *Attorney, Agent, or Firm* — Gavrilovich Dodd & Lindsey LLP; Joseph R. Baker, Jr.

(57) ABSTRACT

Methods and compositions for identifying neoplastic cells in a biological sample are provided.

19 Claims, 10 Drawing Sheets

Figure 1
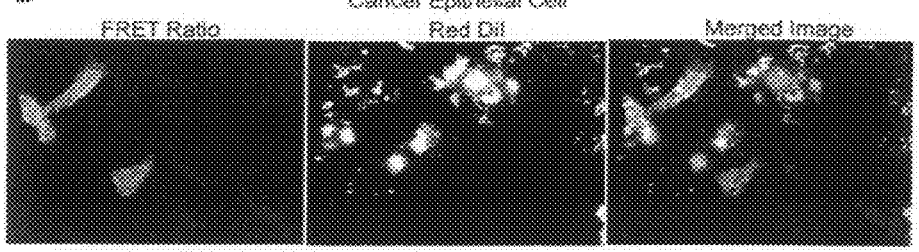
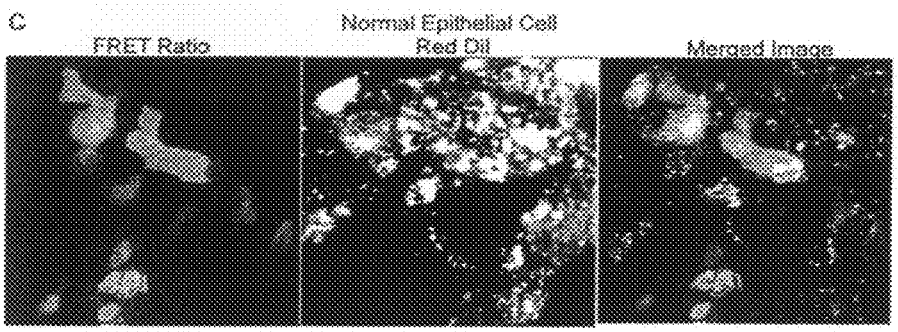
Figure 2
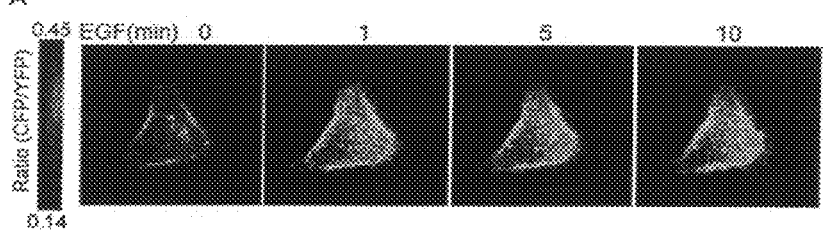
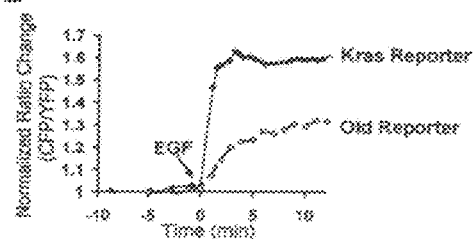

Figure 3A: Sequencing Result of the TAT-Src reporter construct

```
                        His Tag
1/1                  ┌─────────────────┐  31/11
ATG CGG GGT TCT CAT CAT CAT CAT CAT CAT GGT ATG GCT AGC ATG ACT GGT GGA CAG CAA
 M   R   G   S   H   H   H   H   H   H   G   M   A   S   M   T   G   G   Q   Q

┌──────── TAT Tag
61/21                                    91/31
ATG GGT CGG GAT CTG TAC GAC GAT GAC GAT AAG GAT CCG AGG AGG AGG CAG AGG AGG AAG
 M   G   R   D   L   Y   D   D   D   D   K   D   P   R   R   R   Q   R   R   K

─────────────┐  ┌──────► Src Reporter
             │  │                        151/51
AAG AGG GGC ATG GTG AGC AAG GGC GAG GAG CTG TTC ACC GGG GTG GTG CCC ATC CTG GTC
 K   R   G   M   V   S   K   G   E   E   L   F   T   G   V   V   P   I   L   V 81/61                                    211/71
GAG CTG GAC GGC GAC GTA AAC GGC CAC AGG TTC AGC GTG TCC GGC GAG GGC GAG GGC GAT
 E   L   D   G   D   V   N   G   H   R   F   S   V   S   G   E   G   E   G   D 241/81                                   271/91
GCC ACC TAC GGC AAG CTG ACC CTG AAG TTC ATC TGC ACC ACC GGC AAG CTG CCC GTG CCC
 A   T   Y   G   K   L   T   L   K   F   I   C   T   T   G   K   L   P   V   P 301/101                                  331/111
TGG CCC ACC CTC GTG ACC ACC CTG ACC TGG GGC GTG CAG TGC TTC AGC CGC TAC CCC GAC
 W   P   T   L   V   T   T   L   T   W   G   V   Q   C   F   S   R   Y   P   D 361/121                                  391/131
CAC ATG AAG CAG CAC GAC TTC TTC AAG TCC GCC ATG CCC GAA GGC TAC GTC CAG GAG CGT
 H   M   K   Q   H   D   F   F   K   S   A   M   P   E   G   Y   V   Q   E   R 421/141                                  451/151
ACC ATC TTC TTC AAG GAC GAC GGC AAC TAC AAG ACC CGC GCC GAG GTG AAG TTC GAG GGC
 T   I   F   F   K   D   D   G   N   Y   K   T   R   A   E   V   K   F   E   G 481/161                                  511/171
GAC ACC CTG GTG AAC CGC ATC GAG CTG AAG GGC ATC GAC TTC AAG GAG GAC GGC AAC ATC
 D   T   L   V   N   R   I   E   L   K   G   I   D   F   K   E   D   G   N   I 541/181                                  571/191
CTG GGG CAC AAG CTG GAG TAC AAC TAC ATC AGC CAC AAC GTC TAT ATC ACC GCC GAC AAG
 L   G   H   K   L   E   Y   N   Y   I   S   H   N   V   Y   I   T   A   D   K
```

Figure 3B: Sequencing Result of the TAT-Src reporter construct

```
601/201                              631/211
CAG AAG AAC GGC ATC AAG GCC CAC TTC AAG ATC CGC CAC AAC ATC GAG GAC GGC AGC GTG
 Q   K   N   G   I   K   A   H   F   K   I   R   H   N   I   E   D   G   S   V

661/221                              691/231
CAG CTC GCC GAC CAC TAC CAG CAG AAC ACC CCC ATC GGC GAC GGC CCC GTG CTG CTG CCC
 Q   L   A   D   H   Y   Q   Q   N   T   P   I   G   D   G   P   V   L   L   P

721/241                              751/251
GAC AAC CAC TAC CTG AGC ACC CAG TCC AAG CTG AGC AAA GAC CCC AAC GAG AAG CGC GAT
 D   N   H   Y   L   S   T   Q   S   K   L   S   K   D   P   N   E   K   R   D

781/261                              811/271
CAC ATG GTC CTG CTG GAG TTC GTG ACC GCC GCC CGC ATG CAT TGG TAT TTT GGG AAG ATC
 H   M   V   L   L   E   F   V   T   A   A   R   M   H   W   Y   F   G   K   I

841/281                              871/291
ACT CGT CGG GAG TCC GAG CGG CTG CTG CTC AAC CCC GAA AAC CCC CGG GGA ACC TTC TTG
 T   R   R   E   S   E   R   L   L   L   N   P   E   N   P   R   G   T   F   L

901/301                              931/311
GTC CGG GAG AGC GAG ACG ACA AAA GGT GCC TAT TGC CTC
 V   R   E   S   E   T   T   K   G   A   Y   C   L
```

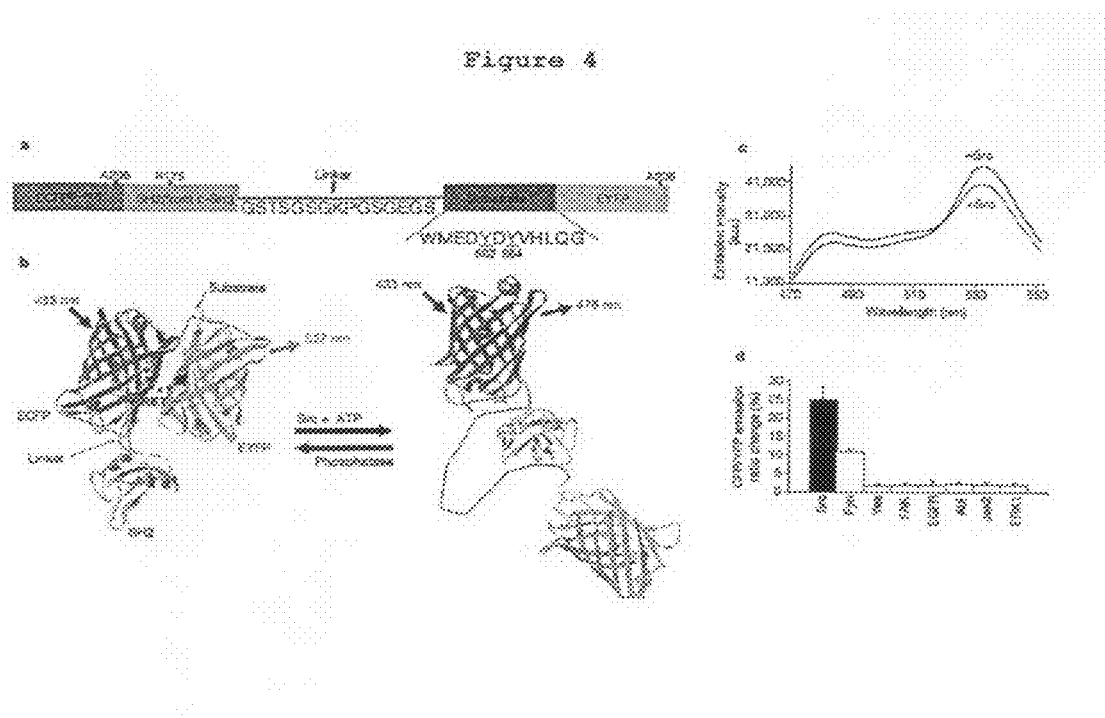

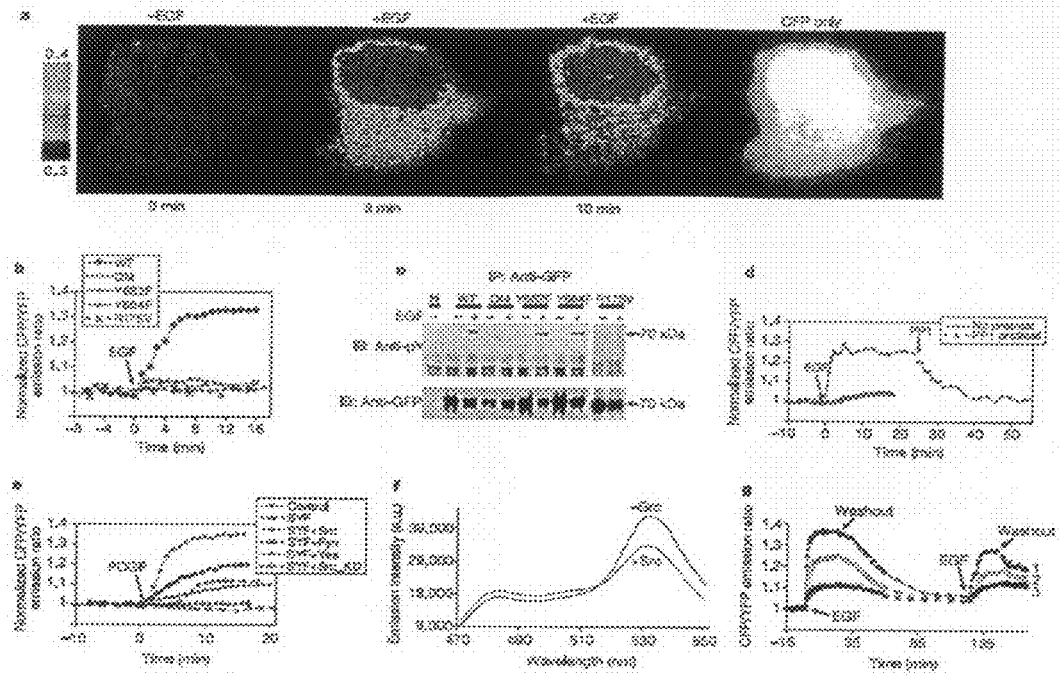

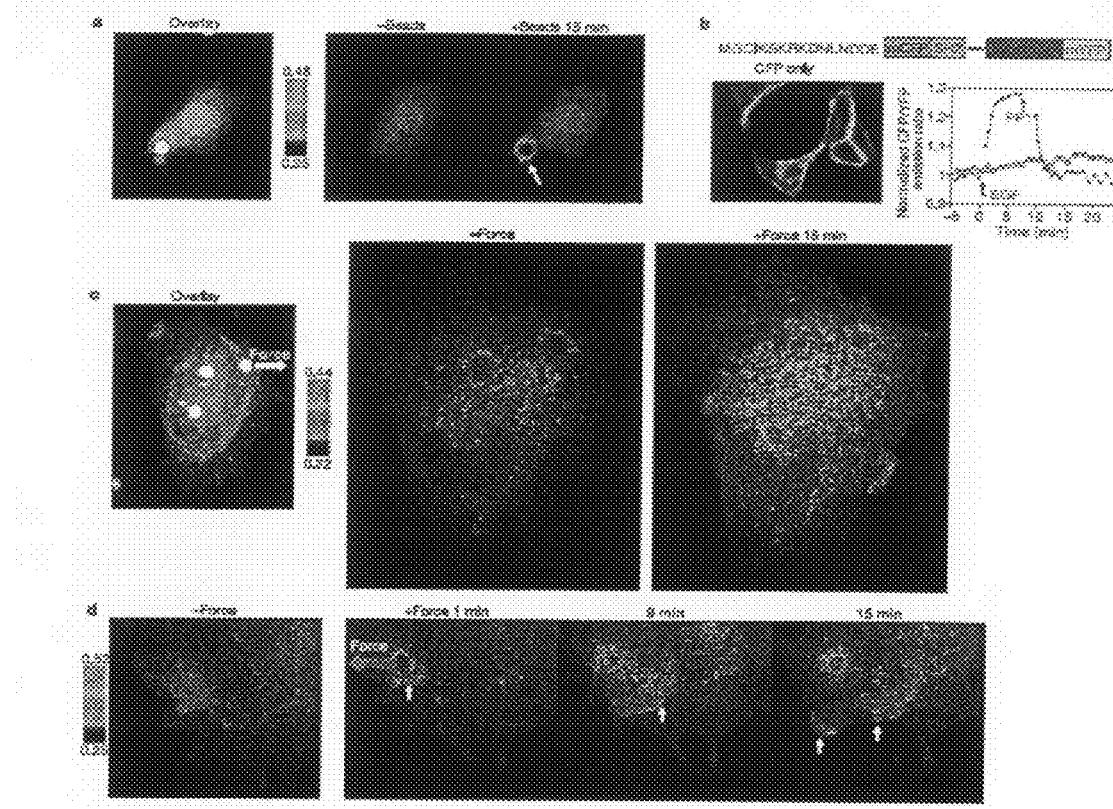

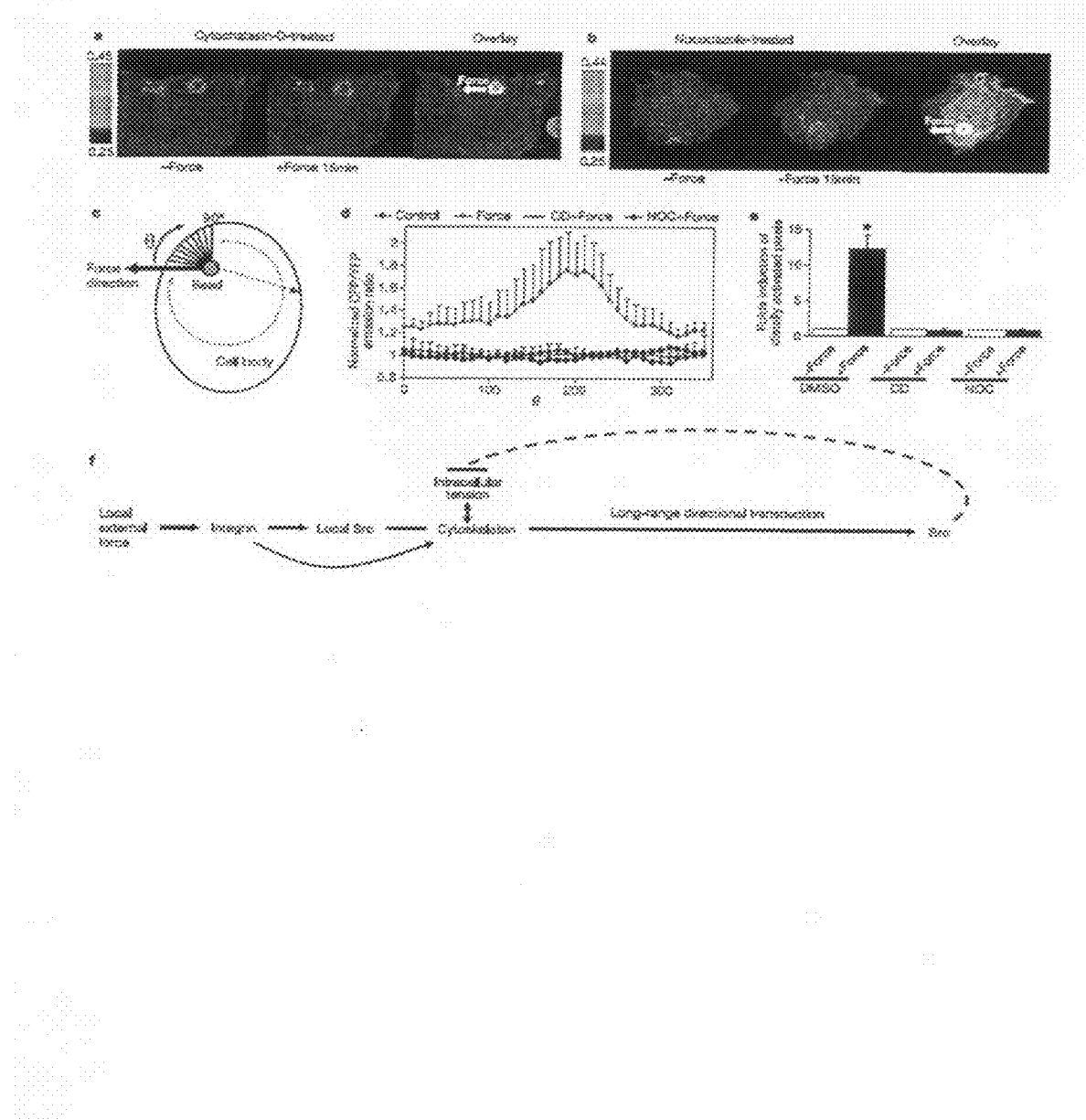

SEQUENCE LISTING

```
<160> NUMBER OF SEQ ID NOS: 6

<210> SEQ ID NO 1
<211> LENGTH: 10
<212> TYPE: PRT
<213> ORGANISM: Artificial Sequence
<220> FEATURE:
<223> OTHER INFORMATION: Peptide translocation domain

<400> SEQUENCE: 1

Arg Arg Arg Gln Arg Arg Lys Lys Arg Gly
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Phosphorylation peptide substrate

<400> SEQUENCE: 2

Trp Met Glu Asp Tyr Asp Tyr Val His Leu Gln Gly
1               5                   10

<210> SEQ ID NO 3
<211> LENGTH: 939
<212> TYPE: DNA
<213> ORGANISM: Artificial Sequence
<220> FEATURE:
<223> OTHER INFORMATION: Fusion construct
<220> FEATURE:
<221> NAME/KEY: CDS
<222> LOCATION: (1)..(939)

<400> SEQUENCE: 3 atg cgg ggt tct cat cat cat cat cat cat ggt atg gct agc atg act      48
Met Arg Gly Ser His His His His His His Gly Met Ala Ser Met Thr
1               5                   10                  15 ggt gga cag caa atg ggt cgg gat ctg tac gac gat gac gat aag gat      96
Gly Gly Gln Gln Met Gly Arg Asp Leu Tyr Asp Asp Asp Asp Lys Asp
                20                  25                  30 ccg agg agg agg cag agg agg aag aag agg ggc atg gtg agc aag ggc     144
Pro Arg Arg Arg Gln Arg Arg Lys Lys Arg Gly Met Val Ser Lys Gly
            35                  40                  45 gag gag ctg ttc acc ggg gtg gtg ccc atc ctg gtc gag ctg gac ggc     192
Glu Glu Leu Phe Thr Gly Val Val Pro Ile Leu Val Glu Leu Asp Gly
        50                  55                  60 gac gta aac ggc cac agg ttc agc gtg tcc ggc gag ggc gag ggc gat     240
Asp Val Asn Gly His Arg Phe Ser Val Ser Gly Glu Gly Glu Gly Asp
65                  70                  75                  80 gcc acc tac ggc aag ctg acc ctg aag ttc atc tgc acc acc ggc aag     288
Ala Thr Tyr Gly Lys Leu Thr Leu Lys Phe Ile Cys Thr Thr Gly Lys
                85                  90                  95
```

```
ctg ccc gtg ccc tgg ccc acc ctc gtg acc acc ctg acc tgg ggc gtg      336
Leu Pro Val Pro Trp Pro Thr Leu Val Thr Thr Leu Thr Trp Gly Val
            100                 105                 110 cag tgc ttc agc cgc tac ccc gac cac atg aag cag cac gac ttc ttc      384
Gln Cys Phe Ser Arg Tyr Pro Asp His Met Lys Gln His Asp Phe Phe
        115                 120                 125 aag tcc gcc atg ccc gaa ggc tac gtc cag gag cgt acc atc ttc ttc      432
Lys Ser Ala Met Pro Glu Gly Tyr Val Gln Glu Arg Thr Ile Phe Phe
130                 135                 140 aag gac gac ggc aac tac aag acc cgc gcc gag gtg aag ttc gag ggc      480
Lys Asp Asp Gly Asn Tyr Lys Thr Arg Ala Glu Val Lys Phe Glu Gly
145                 150                 155                 160 gac acc ctg gtg aac cgc atc gag ctg aag ggc atc gac ttc aag gag      528
Asp Thr Leu Val Asn Arg Ile Glu Leu Lys Gly Ile Asp Phe Lys Glu
                165                 170                 175 gac ggc aac atc ctg ggg cac aag ctg gag tac aac tac atc agc cac      576
Asp Gly Asn Ile Leu Gly His Lys Leu Glu Tyr Asn Tyr Ile Ser His
            180                 185                 190 aac gtc tat atc acc gcc gac aag cag aag aac ggc atc aag gcc cac      624
Asn Val Tyr Ile Thr Ala Asp Lys Gln Lys Asn Gly Ile Lys Ala His
        195                 200                 205 ttc aag atc cgc cac aac atc gag gac ggc agc gtg cag ctc gcc gac      672
Phe Lys Ile Arg His Asn Ile Glu Asp Gly Ser Val Gln Leu Ala Asp
210                 215                 220 cac tac cag cag aac acc ccc atc ggc gac ggc ccc gtg ctg ctg ccc      720
His Tyr Gln Gln Asn Thr Pro Ile Gly Asp Gly Pro Val Leu Leu Pro
225                 230                 235                 240 gac aac cac tac ctg agc acc cag tcc aag ctg agc aaa gac ccc aac      768
Asp Asn His Tyr Leu Ser Thr Gln Ser Lys Leu Ser Lys Asp Pro Asn
                245                 250                 255 gag aag cgc gat cac atg gtc ctg ctg gag ttc gtg acc gcc gcc cgc      816
Glu Lys Arg Asp His Met Val Leu Leu Glu Phe Val Thr Ala Ala Arg
            260                 265                 270 atg cat tgg tat ttt ggg aag atc act cgt cgg gag tcc gag cgg ctg      864
Met His Trp Tyr Phe Gly Lys Ile Thr Arg Arg Glu Ser Glu Arg Leu
        275                 280                 285 ctg ctc aac ccc gaa aac ccc cgg gga acc ttc ttg gtc cgg gag agc      912
Leu Leu Asn Pro Glu Asn Pro Arg Gly Thr Phe Leu Val Arg Glu Ser
290                 295                 300 gag acg aca aaa ggt gcc tat tgc ctc                                   939
Glu Thr Thr Lys Gly Ala Tyr Cys Leu
305                 310

<210> SEQ ID NO 4
<211> LENGTH: 313
<212> TYPE: PRT
<213> ORGANISM: Artificial Sequence
<220> FEATURE:
<223> OTHER INFORMATION: Synthetic Construct

<400> SEQUENCE: 4

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Arg Arg Arg Gln Arg Arg Lys Lys Arg Gly Met Val Ser Lys Gly
        35                  40                  45

Glu Glu Leu Phe Thr Gly Val Val Pro Ile Leu Val Glu Leu Asp Gly
    50                  55                  60

Asp Val Asn Gly His Arg Phe Ser Val Ser Gly Glu Gly Glu Gly Asp
65                  70                  75                  80
```

-continued

```
Ala Thr Tyr Gly Lys Leu Thr Leu Lys Phe Ile Cys Thr Thr Gly Lys
                 85                  90                  95

Leu Pro Val Pro Trp Pro Thr Leu Val Thr Thr Leu Thr Trp Gly Val
            100                 105                 110

Gln Cys Phe Ser Arg Tyr Pro Asp His Met Lys Gln His Asp Phe Phe
        115                 120                 125

Lys Ser Ala Met Pro Glu Gly Tyr Val Gln Glu Arg Thr Ile Phe Phe
    130                 135                 140

Lys Asp Asp Gly Asn Tyr Lys Thr Arg Ala Glu Val Lys Phe Glu Gly
145                 150                 155                 160

Asp Thr Leu Val Asn Arg Ile Glu Leu Lys Gly Ile Asp Phe Lys Glu
                165                 170                 175

Asp Gly Asn Ile Leu Gly His Lys Leu Glu Tyr Asn Tyr Ile Ser His
            180                 185                 190

Asn Val Tyr Ile Thr Ala Asp Lys Gln Lys Asn Gly Ile Lys Ala His
        195                 200                 205

Phe Lys Ile Arg His Asn Ile Glu Asp Gly Ser Val Gln Leu Ala Asp
    210                 215                 220

His Tyr Gln Gln Asn Thr Pro Ile Gly Asp Gly Pro Val Leu Leu Pro
225                 230                 235                 240

Asp Asn His Tyr Leu Ser Thr Gln Ser Lys Leu Ser Lys Asp Pro Asn
                245                 250                 255

Glu Lys Arg Asp His Met Val Leu Leu Glu Phe Val Thr Ala Ala Arg
            260                 265                 270

Met His Trp Tyr Phe Gly Lys Ile Thr Arg Arg Glu Ser Glu Arg Leu
        275                 280                 285

Leu Leu Asn Pro Glu Asn Pro Arg Gly Thr Phe Leu Val Arg Glu Ser
    290                 295                 300

Glu Thr Thr Lys Gly Ala Tyr Cys Leu
305                 310
```

```
<210> SEQ ID NO 5
<211> LENGTH: 15
<212> TYPE: PRT
<213> ORGANISM: Artificial Sequence
<220> FEATURE:
<223> OTHER INFORMATION: Peptide fragment of fusion construct

<400> SEQUENCE: 5

Gly Ser Thr Ser Gly Ser Gly Lys Pro Gly Ser Gly Glu Gly Ser
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Peptide fragment of fusion construct

<400> SEQUENCE: 6

Met Gly Cys Lys Ser Lys Arg Lys Asp Asn Leu Asn Asp Asp Glu
1               5                   10                  15
```

METHODS AND COMPOSITIONS FOR DETECTING NEOPLASTIC CELLS

CROSS REFERENCE TO RELATED APPLICATIONS

This application is filed under 35 U.S.C. §371 and claims priority to International Application Ser. No. PCT/US2006/036143, filed Sep. 15, 2006, which claims priority to U.S. Provisional Application Ser. No. 60/717,599 filed Sep. 15, 2005, the disclosures of which are incorporated herein by reference.

STATEMENTS REGARDING FEDERALLY SPONSORED RESEARCH

The invention was funded in part by a grant awarded by the National Institutes of Health. The government may have certain rights in the invention.

TECHNICAL FIELD

The disclosure relates generally to detection of neoplastic cells and more specifically to methods and compositions for monitoring mechanotransduction in cells.

BACKGROUND

Focal adhesions are specialized structures in the plasma membrane involved in the adhesion of a cell to a substrate, such as the extracellular matrix (ECM). Focal adhesions form the connection between an extracellular substrate and the cytoskeleton, and affect such functions as cell shape, cell motility and cell proliferation. Transmembrane integrin molecules form the basis of focal adhesions. Upon ligand binding, integrins cluster in the plane of the plasma membrane. Cytoskeletal linker proteins such as the actin binding proteins alpha-actinin, talin, tensin, vinculin, paxillin, and filamin are recruited to the clustering site. Key regulatory proteins, such as Rho and Ras family proteins, focal adhesion kinase, and Src family members are also recruited. These events lead to the reorganization of actin filaments and the formation of stress fibers. These intracellular rearrangements promote further integrin-ECM interactions and integrin clustering. Thus, integrins mediate aggregation of protein complexes on both the cytosolic and extracellular faces of the plasma membrane, leading to the assembly of the focal adhesion. Many signal transduction responses are mediated via various adhesion complex proteins, including Src, FAY, paxillin, and tensin (for a review, see Yamada, K. M. and B. Geiger, (1997) Curr. Opin. Cell Biol. 9.76-85.). Src activity plays a key role in the formation of tumors and the development of cancers. In particular, the increased Src activity can be an early event in cancer development, as evidenced in pre-malignant lesions and adenomas. Biosensors that can directly or indirectly detect a change in Src activity provide a mechanism for the early detection of neoplastic cells. To introduce a biosensor into a cell, there are mainly two methods: gene-based and protein-based. The gene-based method requires the introduction of a genetically encoded biosensor into a cell. It takes time for cells to incorporate the biosensors into their genomes and produce encoded proteins through transcription and translation. The low efficiency for transfection methods in general will result in the failure of the identification of non-transfected cancerous cells.

Protein-based methods are similarly limited. The plasma membrane of the cell generally prevents the trespass of polar or large-molecular-weight (>500 Da) molecules. Traditional methods of introducing proteins into the cells involve fusing the desired proteins to receptor ligands or packaging them to liposomal carriers. However, these methods are labor-intensive and usually result in the trapping of desired proteins in endocytic organelles and hence not able to express their proper functions.

Accordingly, methods and compositions for the efficient introduction and detection of biosensors in a living cell are needed.

SUMMARY

Provided herein are compositions and methods for identifying a neoplastic cell. In one embodiment, a chimeric polypeptide including, in operative linkage, a membrane translocation specific domain, a first fluorescent domain, a Src homology domain, a phosphorylatable substrate domain, and a second fluorescent domain, is provided. The polypeptide may further include a lipid membrane destabilization domain such as, for example, hemagglutinin protein (HA2). In another embodiment, the membrane translocation specific domain includes a polypeptide selected from the group consisting of the *drosophila* homeoprotein antennapedia transcription protein, the herpes simplex virus structural protein VP22, and the HIV-1 transcriptional activator Tat protein. The membrane translocation specific domain may include, for example, the amino acid sequence RRRQRRKKRG.

In other embodiments, the first and second fluorescent proteins are selected from the group consisting of green fluorescent proteins (GFPs), red fluorescent proteins (RFPs), cyan fluorescent protein (CFP), monomeric GFP (mGFP), a monomeric CFP (mCFP), yellow fluorescent protein (YFP), monomeric YFP (mYFP), or a spectral variant thereof. In general, the first and the second fluorescent proteins exhibit a detectable resonance energy transfer when the first fluorescent protein is excited.

In another embodiment, at least one amino acid of the phosphorylatable substrate domain is phosphorylated.

In other embodiments, a host cell containing a polypeptide of the invention, and a polynucleotide encoding a polypeptide of the invention, are provided. Also provided are vectors that include a polynucleotide encoding a polypeptide provided herein. In some aspects, a vector of the invention is an expression vector, such as, for example, a bacterial cell, insect cell, or mammalian cell expression vector.

In another embodiment, a host cell containing a polynucleotide of the invention is provided. In other embodiments, kits that include at least one polynucleotide and/or vector and/or polypeptide of the invention are provided.

In another embodiment, methods for identifying a neoplastic cell are provided. Such methods may include transfecting a cell with a polypeptide, polynucleotide or vector of the invention and detecting a change in the fluorescent properties of the polypeptide, or polypeptide expressed from the polynucleotide or vector, in the cell. A change in the fluorescent properties of the polypeptide is indicative of a neoplastic cell.

In another embodiment, a method for identifying a neoplastic cell is provided. The method includes obtaining a biological sample from a subject; introducing a polypeptide of the invention in to a plurality of cells in the sample; contacting the cells with a solid or semi solid substrate that includes fibronectin; scanning the cells with a radiation source suitable for inducing a FRET response; determining the FRET response; and identifying the cells that provide a response indicative of an absence of plasma membrane wave-propagation. In some aspects, the radiation source includes infrared laser-tweezers. In some aspects, the solid or semi solid substrate comprises fibronectin coated beads.

In another embodiment, a system for detecting a cell that includes a biosensor of the invention is provided. The system includes a substrate that includes a biological sample having at least one target cell containing a biosensor. In general the cell is associated with a solid or semi solid substrate that includes an agent that binds to a molecule associated with the cytoskeleton of the cell. The system further includes a detector assembly functionally associated with the substrate and configured to capture images associated with a biosensor polypeptide. The system also includes at least one radiation source coupled to the detector assembly and operationally configured to emit radiation sufficient to subject the solid or semi solid substrate to a mechanical force sufficient to induce a fluorescence resonance energy transfer (FRET) event in the cell. The system also includes a controller operably associated with the detector assembly and radiation source. In general the controller is configured to coordinate radiation emission from the radiation source with the image of the target cell captured by the detector assembly.

In some embodiments, a system provided herein further includes a flow path configured to accommodate the target cell in a fluid. In some aspects, the flow path is fluidly connected with a reservoir comprising a plurality of cells. In some aspects, the flow path is a microfluidic flow path.

In some embodiments, the controller is operated by a user and is configured to determine the ratio of fluorescence resonance energy transfer. In some aspects, the controller is further configured to synchronize entry of a cell in to the flow path. As noted above, the radiation source can a laser suitable for imparting a mechanical force on a particle or substrate, such as a bead.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

FIG. 1, panel A provides a schematic drawing of the design of Src biosensor.

FIG. 1, panel B depicts HeLa cells pre-labeled with the red color DiI were mixed with the non-labeled MDCK cells.

FIG. 1, panel C depicts MDCK cells pre-labeled with the red color DiI mixed with the non-labeled HeLa cells. The mixed cells were transfected with the Src biosensor and serum-starved for 36 hr before being subjected to 5 min of EGF stimulation. Fluorescent images were recorded with a Zeiss inverted fluorescent microscope and a CCD camera. The pixel-wise FRET ratio images of CFP over YFP were generated by Metafluor (the left images), with cold color indicating low Src activity and hot color indicating high levels of activation. The staining in the red color DiI images (the middle images) shows the positions of HeLa cells (see FIG. 1, panel B) or MDCK cells (see FIG. 1, panel C).

FIG. 2, panel A depicts time-lapse FRET ratio images of HeLa cells in response to EGF. The cells were transfected with the Kras-modified Src biosensor and serum-starved with 0.5% FBS medium for 36 hr before being stimulated with 50 ng/ml EGF. The scale bar on the left represents the CFP/YFP ratio.

FIG. 2, panel B is a graph showing HeLa cells were transfected with the Kras-modified Src biosensors or its older version prior to 36 hr serum-starvation and EGF stimulation. The normalized CFP/YFP emission ratios were calculated based on the pixel-wise fluorescence intensity of CFP and YFP emission images.

FIGS. 3A-B depicts a TAT-Src reporter construct nucleic acid and polypeptide sequence (SEQ ID Nos: 3 and 4, respectively).

FIG. 4, panel A depicts the domain structure of Src reporter composed of CFP, the SH2 domain, a flexible linker (SEQ ID NO:5), the Src substrate peptide (SEQ ID NO:2) and YFP.

FIG. 4, panel B illustrates the FRET effect of the Src reporter upon the actions of Src kinase or phosphatase.

FIG. 4, panel c, Emission spectra of the Src reporter before (black) and after (red) phosphorylation by Src.

FIG. 4, panel D depicts in vitro emission ratio changes (mean^s.d.) of the Src reporter in response to Src and other kinases.

FIG. 5, panel A depicts CFP/YFP emission ratio images in response to EGF.

FIG. 5, panel B depicts emission ratio time courses of the Src reporter and its mutants in response to EGF stimulation in HeLa cells.

FIG. 5, panel C depicts tyrosine phosphorylation levels of the various Src reporters. 'N' represents cells without transfection.

FIG. 5, panel D depicts emission ratio time courses of the Src reporter in response to EGF in HeLa cells pretreated with ('PP1 pretreat') or without ('No pretreat') PP1.

FIG. 5, panel E depicts emission ratio time courses of the Src reporter in response to PDGF in MEF and SYF cell lines.

FIG. 5, panel F depicts emission spectra of the monomeric Src reporter before (black) and after (red) in vitro phosphorylation by Src.

FIG. 5, panel G depicts emission ratios of the monomeric Src reporter from three different subcellular regions in HeLa cells stimulated by EGF, followed sequentially by EGF washout, re-stimulation, and a second washout.

FIG. 6, panel A depicts fibronectin-coated bead (white spot from phase contrast image overlaid on CFP cell image) induced FRET responses around the bead. White arrow points to the spot with activated Src. Color bar represents CFP/YFP emission ratio values.

FIG. 6, panel B depicts a schematic diagram showing the design strategy of membrane targeting (SEQ ID NO:6). The CFP- only image on the left shows the effective tethering of the reporter on the plasma membrane. The EGF-induced FRET responses of the reporter is reversed by PPI (red line) and prevented by pretreatment with PPI (blue line).

FIG. 6, panel C depicts laser-tweezer traction on the bead at the upper right corner of the cell (shown on the left) caused FRET responses. White arrow represents force direction.

FIG. 6, panel D depicts FRET responses of a cell with clear directional wave propagation away from the site of mechanical stimulation.

FIG. 7, panel A depicts emission ratio images of HUVECs pretreated with cytochalasin D before and after force application.

FIG. 7, panel B depicts emission ratio images of HUVECs pretreated with nocodazole before and after force application.

FIG. 7, panel C depicts a schematic drawing of the polarity analysis strategy.

FIG. 7, panel D depicts polarity analysis (mean^s.d.) of the force-induced FRET response. Control, no force application. CD or NOC, cytochalasin D or nocodazole treatment, respectively.

FIG. 7, panel E depicts HUVECs treated with cytochalasin D, nocodazole or DMSO were subjected to mechanical force for 15 min or kept as static control. Bar graphs represent mean^s.d. of the force-induced fold induction of distally activated (see Methods, with 80% threshold) pixel numbers. The asterisk indicates a significant difference (P, 0.05) before and after force application.

FIG. 7, panel F depicts a mechanism by which local mechanical forces can induce directional and long-range Src activations.

FIG. 10, panel B provides images of polylysine-coated beads incubated for 20 min with HUVECs expressing the Src reporter, as indicated by the image on the far right. Laser-tweezers were turned on and off intermittently and the motions of the polylysine-coated bead were recorded to visually demonstrate that the laser-tweezer-traction can be effectively applied to beads. A steady laser-tweezer-traction was then used to mechanically pull the bead towards the left.

FIG. 11, panel B provides images of HeLa cells expressing the membrane-targeted Src reporter pretreated with PP1 (10 uM) for 1 hr before subjected to EGF (50 ng/ml). The time-lapse emission ratio images are shown on the left and the CFP-only image is shown on the far right.

FIG. 13, panel B provides images indicating that mechanical forces on fibronectin-coated beads did not induce FRET responses of inactive mutant R175V of the membrane-targeted Src reporter. Fibronectin-coated beads were incubated with HUVECs expressing the mutant R175V of the membrane-targeted Src reporter, as indicated by the images on the far right. Laser-tweezers were used to apply a steady 300-pN mechanical force (towards the right) on the bead. The time-lapse CFP/YFP emission ratio images of the cells correspond to before and after force application are shown on the left as indicated.

Like reference symbols in the various drawings indicate like elements.

DETAILED DESCRIPTION

Figure 8:
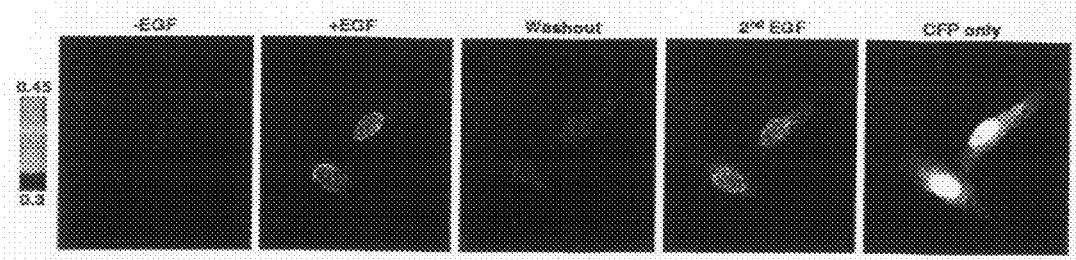
FIG. 8 provides images indicating that the monomeric Src reporter has a better dynamic range and is reversible. HeLa cells transfected with the Src reporter were subjected to various treatments as indicated. The representative emission ratio images are shown on the left and the CFP-only image is shown on the far right.

Biosensor to detect Src activity with high sensitivity, especially with temporal and spatial resolution, will not only advance our understanding of the molecular mechanism of the Src activation, but also provide a powerful tool to diagnose and evaluate the early cancer development in human body. Accordingly, provided herein are systems, methods and compositions for the fast introduction of a protein-based Src biosensor into cells for the early identification of cancerous cells. Systems for detecting a biosensor in a cell are also provided.

U.S. Pat. No. 6,900,304, U.S. patent application Ser. No. 09/865,291, and U.S. patent application Ser. No. 10/857,622 are incorporated herein by reference, in their entirety, for all purposes. All patents and publications mentioned in the specification are indicative of the levels of skill of those skilled in the art to which the invention pertains. All references cited in this disclosure are incorporated by reference to the same extent as if each reference had been incorporated by reference in its entirety individually. Unless specifically indicated otherwise, all technical and scientific terms used herein have the same meaning as commonly understood by those of ordinary skill in the art to which this invention belongs. In addition, any method or material similar or equivalent to a method or material described herein can be used in the practice the present invention. For purposes of the present invention, the following terms are defined.

In a first embodiment, an isolated chimeric polypeptide is provided. The polypeptide includes, in operative linkage, a membrane translocation specific domain, a first fluorescent domain, a Src homology domain, a phosphorylatable substrate domain, and a second fluorescent domain. In general, the first and the second fluorescent proteins are different.

The term "operatively linked," "in operative linkage" or "operatively associated" also is used herein to indicate that the components of a biosensor (sometimes referred to as a Src biosensor) are joined together such that each component maintains its function relevant to phosphorylation detection, or can be induced to express its function. For example, the phosphorylatable substrate domain is operatively linked to the SH2 domain such that, when an amino acid residue of the phosphorylatable substrate domain is phosphorylated, the substrate peptide can bind to the phosphopeptide-binding pocket of the SH2 domain and separate the first fluorescent domain from the second fluorescent domain, thus decreasing the FRET. The loss of FRET is consistent with intramolecular complexation of the phosphorylated substrate with the SH2 domain and the consequent disruption of the close apposition of the first and second fluorescent domains. Methods for operatively linking the components of a biosensor, including the use of linker and spacer peptides and the like, can be determined rationally based, for example, on crystallographic information, can be extrapolated from the methods and compositions disclosed herein, or can be determined empirically. A linker molecule may be, for example, a polypeptide, and be capable of forming an operative linkage between other moieties. Linker polypeptides may have lengths, for example, of between about 3 amino acid residues to about 50 amino acid residues, or between about 4 amino acid residues to about 30 amino acid residues, or between about 5 amino acid residues to about 15 amino acid residues.

The term "signal transduction pathway" refers to the molecules that propagate an extracellular signal through the cell membrane to become an intracellular signal. This signal can then stimulate a cellular response. The polypeptide molecules involved in signal transduction processes are typically receptor and non-receptor protein tyrosine kinases, receptor and non-receptor protein phosphatases, polypeptides containing SRC homology 2 and 3 domains, phosphotyrosine binding proteins (SRC homology 2 (SH2) and phosphotyrosine binding (PTB and PH) domain containing proteins), proline-rich binding proteins (SH3 domain containing proteins), GTPases, phosphodiesterases, phospholipases, prolyl isomerases, proteases, $Ca^{2+}$ binding proteins, cAMP binding proteins, guanyl cyclases, adenylyl cyclases, NO generating proteins, nucleotide exchange factors, and transcription factors.

Many growth factor receptors, including receptors for epidermal growth factor, platelet-derived growth factor, fibroblast growth factor, as well as the growth modulator alpha-thrombin, contain intrinsic protein kinase activities. When growth factor binds to the receptor, it triggers the autophosphorylation of a serine, threonine, or tyrosine residue on the receptor. These phosphorylated sites are recognition sites for the binding of other cytoplasmic signaling proteins. These proteins participate in signaling pathways that eventually link the initial receptor activation at the cell surface to the activation of a specific intracellular target molecule. In the case of tyrosine residue autophosphorylation, these signaling proteins contain a common domain referred to as a "Src homology" (SH) domain. SH2 domains and SH3 domains are found in phospholipase C-gamma, PI-3-K p85 regulatory subunit, Ras-GTPase activating protein, and pp 60.sup.c-src (Lowenstein, E. J. et al. (1992) Cell 70:431-442).

It is understood that the components of a chimeric polypeptide provided herein can be operatively inserted in to a polypeptide of the invention in any order suitable for use of the polypeptide as a biosensor. The term "operatively inserted" is used herein to refer to the introduction of a first polypeptide into a second polypeptide, at a position between the N-terminus and C-terminus of the second polypeptide, such that each of the polypeptides maintains its original function or can be induced to express its original function. For example, where a phosphorylatable substrate is operatively inserted into a fluorescent protein, the phosphorylatable polypeptide maintains its ability to act as a substrate for a phosphatase or kinase, and the fluorescent protein maintains its characteristic fluorescence property, although the fluorescence property may not be exhibited due, for example, to the phosphorylation state of the phosphorylatable polypeptide.

The term "polypeptide" or "protein" refers to a polymer of two or more amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "isolated" or "purified" refers to a material that is substantially or essentially free from components that normally accompany the material in its native state in nature. Purity or homogeneity generally are determined using analytical chemistry techniques such as polyacrylamide gel electrophoresis, high performance liquid chromatography, and the like. A polynucleotide or a polypeptide is considered to be isolated when it is the predominant species present in a preparation. Generally, an isolated protein or nucleic acid molecule represents greater than 80% of the macromolecular species present in a preparation, often represents greater than 90% of all macromolecular species present, usually represents greater than 95%, of the macromolecular species, and, in particular, is a polypeptide or polynucleotide that purified to essential homogeneity such that it is the only species detected when examined using conventional methods for determining purity of such a molecule.

In general, fluorescent proteins include proteins such as green fluorescent proteins (GFPs), red fluorescent proteins (RFPs), cyan fluorescent protein (CFP), monomeric GFP (mGFP), a monomeric CFP (mCFP), yellow fluorescent protein (YFP), monomeric YFP (mYFP), or a spectral variant thereof. It is understood that the first and the second fluorescent proteins of the chimeric polypeptide exhibit a detectable resonance energy transfer when the first fluorescent protein is excited.

Fluorescent molecules are useful in fluorescence resonance energy transfer, FRET, which involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should be as high as possible to maximize Ro, which represents the distance at which energy transfer efficiency is 50%. However, the excitation spectra of the donor and acceptor should overlap as little as possible so that a wavelength region can be found at which the donor can be excited efficiently without directly exciting the acceptor because fluorescence arising from direct excitation of the acceptor can be difficult to distinguish from fluorescence arising from FRET. Similarly, the emission spectra of the donor and acceptor should overlap as little as possible so that the two emissions can be clearly distinguished. High fluorescence quantum yield of the acceptor moiety is desirable if the emission from the acceptor is to be measured either as the sole readout or as part of an emission ratio. One factor to be considered in choosing the donor and acceptor pair is the efficiency of fluorescence resonance energy transfer between them. The efficiency of FRET between the donor and acceptor is at least 10%, or at least 25%, or at least 50%, preferably at least 75%, more preferably at least 80%, more preferably still at least 85%, even more preferably at least 85%, and more preferably still at least 90%.

The term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between wild type *Aequorea* GFP and a spectral variant, or a mutant thereof, is useful. A measurable difference can be determined by determining the amount of any quantitative fluorescent property, e.g., the amount of fluorescence at a particular wavelength, or the integral of fluorescence over the emission spectrum. Determining ratios of excitation amplitude or emission amplitude at two different wavelengths ("excitation amplitude ratioing" and "emission amplitude ratioing", respectively) are particularly advantageous because the ratioing process provides an internal reference and cancels out variations in the absolute brightness of the excitation source, the sensitivity of the detector, and light scattering or quenching by the sample.

As used herein, the term "fluorescent protein" refers to any protein that can fluoresce when excited with an appropriate electromagnetic radiation, except that chemically tagged proteins, wherein the fluorescence is due to the chemical tag, and polypeptides that fluoresce only due to the presence of certain amino acids such as tryptophan or tyrosine, which fluoresce when exposed to ultraviolet light, are not considered fluorescent proteins for purposes of the present invention. In general, a fluorescent protein useful for preparing a composition of the invention or for use in a method of the invention is a protein that derives its fluorescence from autocatalytically forming a chromophore. A fluorescent protein can contain amino acid sequences that are naturally occurring or that have been engineered (i.e., variants or mutants). When used in reference to a fluorescent protein, the term "mutant" or "variant" refers to a protein that is different from a reference fluorescent protein. *Aequorea* GFP is widely used in cell biology as a protein module that can be fused to host proteins to make the latter fluorescent (Tsien, Ann. Rev. Biochem. 67:509-544, 1998). For example, GFP is commonly used to characterize subcellular localization and trafficking properties of proteins, to which the GFP is fused. For example, a spectral variant of *Aequorea* GFP can be derived from the naturally occurring GFP by engineering mutations such as amino acid substitutions into the reference GFP protein. For example ECFP is a spectral variant of GFP that contains substitutions with respect to GFP. Other spectral variants include, for example, EGFP and EYFP.

Many cnidarians use green fluorescent proteins as energy transfer acceptors in bioluminescence. The term "green fluorescent protein" is used broadly herein to refer to a protein that fluoresces green light, for example, *Aequorea* GFP. GFPs have been isolated from the Pacific Northwest jellyfish, *Aequorea victoria*, the sea pansy, *Renilla reniformis*, and *Phialidium gregarium* (Ward et al., Photochem. Photobiol. 35:803-808, 1982; Levine et al., Comp. Biochem. Physiol. 72B:77-85, 1982). Similarly, reference is made herein to "red fluorescent proteins", which fluoresce red, "cyan fluorescent proteins," which fluoresce cyan, and the like. RFPs, for example, have been isolated from the coral, Discosoma.

A variety of *Aequorea* GFP-related fluorescent proteins having useful excitation and emission spectra have been engineered by modifying the amino acid sequence of a naturally occurring GFP from *A. victoria* (see Prasher et al., Gene 111:229-233, 1992; Heim et al., Proc. Natl. Acad. Sci., USA 91:12501-12504, 1994; U.S. Ser. No. 08/337,915, filed Nov. 10, 1994; International application PCT/US95/14692). As used herein, reference to a "related fluorescent protein" refers to a fluorescent protein that has a substantially identical amino acid sequence when compared to a reference fluorescent protein. In general, a related fluorescent protein, when compared to the reference fluorescent protein sequence, has a contiguous sequence of at least about 150 amino acids that shares at least about 85% sequence identity with the reference fluorescent protein, and particularly has a contiguous sequence of at least about 200 amino acids that shares at least about 95% sequence identity with the reference fluorescent protein. Thus, reference is made herein to an "*Aequorea*-related fluorescent protein" or to a "GFP-related fluorescent protein," which is exemplified by the various spectral variants and GFP mutants that have amino acid sequences that are substantially identical to *A. Victoria* GFP, to a "Discosoma-related fluorescent protein" or a "DsRed-related fluorescent related protein," which is exemplified by the various mutants that have amino acid sequences substantially identical to that of DsRed, and the like, for example, a *Renilla*-related fluorescent protein or a Phialidium-related fluorescent protein.

Some fluorescent proteins have a reduced propensity to oligomerize as compared to a naturally occurring amino acid sequence or to a particular synthetic amino acid sequence. Such fluorescent proteins may be termed "non-oligomerizing proteins" or "non-oligomerizing fluorescent proteins."

A chimeric polypeptide provided herein includes membrane translocation specific domains such as the *drosophila* homeoprotein antennapedia transcription protein, the herpes simplex virus structural protein VP22, and the HIV-1 transcriptional activator Tat protein. In some aspects, the membrane translocation specific domain includes the amino acid sequence RRRQRRKKRG (SEQ ID NO:1). A chimeric polypeptide further includes a phosphorylatable substrate domain that includes the amino acid sequence WMEDYDYVHLQG (SEQ ID NO:2).

In some embodiments, a biosensor comprising a chimeric polypeptide provided herein further includes a lipid membrane destabilization domain. An exemplary lipid destabilization domain includes hemagglutinin protein (HA2).

It is understood that a chimeric polypeptide provided herein includes amino acid sequence(s) that can tolerate amino acid substitutions without impacting or eliminating the function of a particular domain. Accordingly, the present invention encompasses polypeptides that are not identical in amino acid sequence to a chimeric polypeptide of the invention but do have functional identity to a chimeric polypeptide.

The term "identical," when used in reference to two or more polynucleotide sequences or two or more polypeptide sequences, refers to the residues in the sequences that are the same when aligned for maximum correspondence. When percentage of sequence identity is used in reference to a polypeptide, it is recognized that one or more residue positions that are not otherwise identical can differ by a conservative amino acid substitution, in which a first amino acid residue is substituted for another amino acid residue having similar chemical properties such as a similar charge or hydrophobic or hydrophilic character and, therefore, does not change the functional properties of the polypeptide. Where polypeptide sequences differ in conservative substitutions, the percent sequence identity can be adjusted upwards to correct for the conservative nature of the substitution. Such an adjustment can be made using well known methods, for example, scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using any well known algorithm (see, for example, Meyers and Miller, Comp. Appl. Biol. Sci. 4:11-17, 1988; Smith and Waterman, Adv. Appl. Math. 2:482, 1981; Needleman and Wunsch, J. Mol. Biol. 48:443, 1970; Pearson and Lipman, Proc. Natl. Acad. Sci., USA 85:2444 (1988); Higgins and Sharp, Gene 73:237-244, 1988; Higgins and Sharp, CABIOS 5:151-153; 1989; Corpet et al., Nucd. Acids Res. 16:10881-10890, 1988; Huang, et al., Comp. Appl. Biol. Sci. 8:155-165, 1992; Pearson et al., Meth. Mol. Biol., 24:307-331, 1994). Alignment also can be performed by simple visual inspection and manual alignment of sequences.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a non-oligomerizing fluorescent protein also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein. Furthermore, it will be recognized that individual substitutions, deletions or additions that alter, add or delete a single amino acid or a small percentage of amino acids (typically less than 5%, and generally less than 1%) in an encoded sequence can be considered conservatively modified variations, provided alteration results in the substitution of an amino acid with a chemically similar amino acid. Conservative amino acid substitutions providing functionally similar amino acids are well known in the art.

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity. One protein or polypeptide is related to another protein or polypeptide where the proteins are substantially identical or substantially similar. Thus, for example, one protein or polypeptide is related to another protein or polypeptide where the amino acid sequences of the proteins or polypeptides have for example, at least 85% sequence identity. Similarly, two or more proteins or polypeptides may be termed related proteins or polypeptides if they share at least 90% sequence identity. In addition, two or more proteins or polypeptides may be termed related proteins or polypeptides if they share at least 95% sequence identity, or if they share at least 99% sequence identity. Thus, for example, a protein related to a GFP is a protein having an amino acid sequence having at least 85% sequence identity, or at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, or at least 99% sequence identity, with the amino acid sequence of GFP.

It is also understood that the invention includes polynucleotides that encode the polypeptides of the invention. The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. It will be understood that when a nucleic acid molecule is represented by a DNA sequence, this also includes RNA molecules having the corresponding RNA sequence in which "U" replaces "T."

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a chimeric phosphorylation indicator of the invention linked to a polypeptide of interest such as a cell compartmentalization domain. The term "recombinant host cell" refers to a cell that contains a recombinant nucleic acid molecule. As such, a recombinant host cell can express a polypeptide from a "gene" that is not found within the native (non-recombinant) form of the cell.

Reference to a polynucleotide "encoding" a polypeptide means that, upon transcription of the polynucleotide and translation of the mRNA produced therefrom, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

The term "expression control sequence" refers to a nucleotide sequence that regulates the transcription or translation of a polynucleotide or the localization of a polypeptide to which to which it is operatively linked. Expression control sequences are "operatively linked" when the expression control sequence controls or regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a STOP codon, a ribosome binding site, or a sequence that targets a polypeptide to a particular location, for example, a cell compartmentalization signal, which can target a polypeptide to the cytosol, nucleus, plasma membrane, endoplasmic reticulum, mitochondrial membrane or matrix, chloroplast membrane or lumen, medial trans-Golgi cisternae, or a lysosome or endosome, or is a membrane translocating peptide, which allows a molecule operatively linked thereto to cross a cell membrane and enter an intact cell. Cell compartmentalization domains are well known in the art and include, for example, a peptide containing amino acid residues 1 to 81 of human type II membrane-anchored protein galactosyltransferase, or amino acid residues 1 to 12 of the presequence of subunit IV of cytochrome c oxidase (see, also, Hancock et al., EMBO J. 10:4033-4039, 1991; Buss et al., Mol. Cell. Biol. 8:3960-3963, 1988; U.S. Pat. No. 5,776,689).

The present invention provides compositions and methods that are generally useful for non-destructively detecting and monitoring protein kinase and phosphatase activities and protein-protein interactions in individual living eukaryotic cells, including mammalian cells, and provide a means to obtain spatial and temporal resolution on the order of a few micrometers and seconds, or better. As disclosed herein, protein kinase and phosphatase activities can be monitored using biosensors that incorporate reporter molecules such as fluorescent proteins or luminescent complexes, whose properties change significantly as a function of the phosphorylation state of the substrate. Protein interactions are detected by resonance energy transfer using fluorescent proteins or lanthanide complexes to label the putative partners. The compositions of the invention are adaptable to modification using methods such as high throughput combinatorial generation and screening techniques and, therefore, readily can be varied to allow monitoring of any desired kinase, phosphatase, or protein interaction.

The recently discovered *drosophila* homeoprotein antennapedia transcription protein, the herpes simplex virus structural protein VP22, and the HIV-1 transcriptional activator Tat protein have been shown to lead their fused target proteins into cells. For example, Tat can lead cargo proteins into the cells with a 100% efficiency independent of cell types in minutes without causing cell toxicity. However, Tat-fused proteins can also be sequestered in macropinosomes. Recent studies have shown that the influenza virus hemagglutinin protein (HA2) is pH sensitive and can destabilize the lipid membrane when the surrounding pH is low. The co-introduction of the 20 N-terminal amino acids of HA2 has been shown to disrupt the macropinosomes due to low pH and release the trapped Tat-fused proteins into the cytoplasm. Therefore, provided herein are protein-based methods and compositions for delivery and detection of Src biosensors in cells. Such methods and compositions can be used to detect neoplastic cells with accuracy and high speed.

Fluorescence resonance energy transfer (FRET) occurs when two fluorophores are in proximity, with the emission spectrum of the donor overlapping the excitation spectrum of the acceptor. Any change of the distance and/or relative orientation between the two fluorophores can affect the efficiency of FRET and therefore the ratio of acceptor to donor emissions. Previous studies have shown that fusion proteins with interacting peptide partners sandwiched between two fluorescent proteins with different colors are capable of monitoring various cellular events in live cells with high spatial and temporal resolution. In this proposal, a FRET-based biosensor will be applied to detect the Src activity in live normal and cancer cells.

The methods and compositions provided herein combine FRET technology with genetically encoded Src biosensors enabling the visualization of Src activity in live cells with high temporal and spatial resolution. Because the activity of Src, the first protein tyrosine kinase discovered, is closely correlated with early carcinogenesis, it was proposed to apply this gene-based Src reporter for the detection of early cancer development in live cells in biopsy samples. Proof-of-principle studies have demonstrated that this gene-based Src biosensor can accurately identify cancer cells mixed with normal cells.

This genetically encoded reporter requires transfection to be introduced into cells and the production of encoded proteins through transcription and translation. Thus, there are several disadvantages to this method for usage in cancer diagnosis. First, the transduction efficiency is relatively low (10-50% of cells), and this may result in the failure of the identification of non-transfected cancerous cells. Second, the protein expression levels vary among transfected cells. Finally, the long-time in vitro culture complicates the procedure of tissue sample maintenance and, most importantly, may affect the cellular functions of the samples, thus decreasing the accuracy of the signals detected by the biosensor.

Recent studies have revealed that HIV-1 tat protein can pass across the plasma membrane and deliver cargo proteins into cells through macropinocytosis in a few minutes. A small peptide derived from the influenza virus hemagglutinin protein (HA2) has been further shown to facilitate the release of the cargo proteins from macropinosomes into cytoplasm to become biologically functional.

Novel compositions and methods for the early and fast detection of cancer cells with improved sensitivity and reliability are provided herein. It is commonly recognized that the early detection of cancer is crucial for its ultimate control and prevention. For cervical cancer diagnostics, there are about 55-million Pap smear tests performed every year in the United States. However, Pap test is prone to errors at all levels, including sample collection, data examination and interpretation, and has a high number of false-negative results (20-40%). In particular, it remains a great challenge for cytologists to precisely determine the cellular status based on the morphological criteria. For example, one type of cells is described as "atypical glandular cells of undetermined significance" (AGUS), in which 40% of these cells are found to be dysplastic or cancerous after further costly and invasive examinations. Therefore, it is of great interest to develop a better method to analyze the samples collected in a Pap test with a higher sensitivity and accuracy. Src is a key molecule in oncogenesis and plays a major role in early cancer development and progression. Previously developed gene-based Src biosensor have been shown to precisely identify transfected cervical cancer cells among surrounding normal cells, but it is unable to identify non-transfected cancer cells. The development of a 100% efficient and fast method for the delivery of the Src biosensor into cells may allow the precise and convenient diagnosis of every single cervical cancer cell at its early stage with a Pap test sample. This protein-based TAT-HA2 method can be performed alone or in combination with a standard Pap test to reduce the false-negative rate.

In addition to its importance in regulating cervical cancer development, Src activity also plays crucial roles in the development of breast cancer, colon cancer, pancreatic cancer, lung cancer, and many other types of cancers (4). Therefore, our TAT-HA2 mediated biosensor cancer-detection method will have wide-spread usage in clinical diagnostics for many other types of cancers.

The plasma membrane of the cell is a barrier preventing the entrance of macromolecules into the cytoplasm. The protein-based Src biosensor provided herein can be introduced into cells by TAT through macropinocytosis and released into the cytoplasm by the accompanied HA2 due to their low pH. With a previously-prepared stock solution of bacteria-produced Src biosensor protein, the whole process can be completed in a short period of time with high efficiency of protein introduction. A uniform biosensor concentration among cells can also be conveniently achieved. The integration of the present protein-based TAT-HA2 method with previously developed FRET-based technology provides a novel approach for rapid and accurate screening of cancerous cells in biopsy samples.

An exemplary biosensor of the invention can include a Src substrate peptide derived from p130cas and its binding partner, a SH2 domain derived from Src, fused and sandwiched between a N-terminal CFP and a C-terminal YFP (see FIG. 1, panel A). Upon Src activation and the subsequent tyrosine phosphorylation of the substrate peptide, the SH2 domain binds to the phosphorylated substrate and causes a change in the topographical relation between CFP and YFP and alter the FRET. The CFP/YFP emission ratio provides a dynamic readout of Src activities with high spatial and temporal resolution. The Src biosensors were transfected into a mixture of HeLa cells (cancer epithelial cell line) and MDCK cells (normal epithelial cell line). The FRET imaging can accurately identify HeLa cells among MDCK cells, confirmed by the co-labeling of one or the other cell type with the red color DiI. The FRET ratio in HeLa cells is significantly higher than that in MDCK cells (FIG. 1, panel B and panel C). This provides an accurate criterion for distinguishing the cancer cells from normal cells.

In another embodiment, the sensitivity of the detection can be enhanced by fusing a Kras peptide at C-terminal end of a Src biosensor. The normalized CFP/YFP emission ratio change of this exemplary biosensor upon EGF stimulation is about 60%. FIG. 2, panel A shows that EGF causes a rapid enhancement of CFP/YFP emission ratio in HeLa cells. FIG. 2, panel B shows the quantified results comparing the CFP/YFP emission ratio changes of the new Kras-modified Src biosensor versus its old version.

A biosensor capable of detecting the specific Src kinase activity in live cells is provided herein. Upon force application, e.g., by using laser-tweezers, a wave propagation of Src activation along plasma membrane may be observed in a cell, which is dependent on the integrity of actin-network and microtubules. This phenomenon provides an approach that can be used to differentiate normal cells and cytoskeleton-altered diseased cells (e.g., neoplastic cells).

Methods and compositions provided herein may be used to detect the early stage of disease development, which can be represented by abnormal propagation of Src activation even in very few diseased cells among all the cells in a biopsy sample. In addition, the methods and compositions may be used to detect the disease development in live cells, and hence avoids any artificial distortion of the cell system introduced by existing assays which are destructive to the cells. Also provided are high temporal and spatial resolutions in monitoring progress of diseases. Furthermore, the present invention provides continuous, nondestructive assay of wave-propagation of Src activation in cells or subcompartments of cells, and thus is ideally suited for screening of drug candidates.

The Src biosensor may be transfected into live biopsy cell samples, followed by the addition of fibronectin-coated beads. Infrared laser-tweezers may scan through the entire biopsy sample and mechanically perturb the beads in the scan path. At the same time, the CFP and YFP Images will be recorded and FRET images will be computed. If there is an absence of wave propagation in any mechanically-perturbed cell, the biopsy sample will be identified as having abnormal cells and subjected to further examination.

Thus, an exemplary method of the invention may include: 1) transfecting the membrane-targeted Src biosensor into biopsy samples; 2) contacting fibronectin-coated beads with the transfected biopsy samples; 3) scanning through the whole sample with infrared laser-tweezers; 4) recording the FRET response of the biopsy samples; and 5) identifying the cells without wave-propagation.

Mechanical stimuli activate integrins and the cytoskeleton to regulate cellular functions such as movement and adhesion. When activated, integrins associate with Src via its SH3 domain, thus unmasking the Src kinase domain and activating Src. Src can regulate integrin-cytoskeleton interaction, and cause dissolution of actin stress fibers and the release of mechanical tensile stress.

The mechanical environment crucially influences many cell functions. However, it remains largely mysterious how mechanical stimuli are transmitted into biochemical signals. Src is known to regulate the integrin-cytoskeleton interaction, which is essential for the transduction of mechanical stimuli. Using fluorescent resonance energy transfer (FRET), the Src biosensor provided herein enables the imaging and quantification of spatio-temporal activation of Src in live cells.

Local mechanical stimulation can be achieved by any method know to the skilled artisan. One exemplary method includes the use of laser-tweezer traction on fibronectin-coated beads adhering to cells that include a Src biosensor. Rapid distal Src activation and a slower directional wave propagation of Src activation along the plasma membrane is detectable using this method. This wave propagated away from the stimulation site with a speed (mean 6 s.e.m.) of 18.1 6 1.7 nm s. This force-induced directional and long-range activation of Src was abolished by the disruption of actin filaments or microtubules. The biosensor allows for the monitoring of mechanotransduction in live cells with spatio-temporal characterization. The transmission of mechanically induced Src activation is a dynamic process that directs signals via the cytoskeleton to spatial destinations.

A Src substrate peptide (WMEDYDYVHLQG (SEQ ID NO:2), derived from a primary in vivo c-Src substrate-molecule pl30casll, 12) was designed to provide sufficient space for Src to gain access (FIG. 4, panel A). The proximity of the N and C terminals of the SH2 domain, revealed by its crystal structureIδ, allows for the juxtaposition of cyan and yellow fluorescent proteins (CFP and YFP) to yield a high FRET. Upon Src phosphorylation, the substrate peptide can bind to the phosphopeptide-binding pocket of the SH2 domain and separate YFP from CFP, thus decreasing the FRET (FIG. 4, panel B). Phosphorylation of the purified reporter by Src in vitro enhanced CFP emission at the expense of YFP emission (FIG. 4, panel C) and increased the cyan-to-yellow emission ratio by 25%, indicating a Src-induced loss of FRET. The emission ratio changed for other kinases (Yes, FAK, EGFR, Abl, Jak2 or Ser/Thr kinase ERKI) and changed moderately (about 10%) only for Fyn, a close relative of Src (FIG. 4, panel D). The Src-induced loss of FRET is consistent with intramolecular complexation of the phosphorylated substrate with the SH2 domain and the consequent disruption of the close apposition of the CFP and YFP domains (FIG. 4, panel B).

Accordingly, in another embodiment, a method for identifying a neoplastic cell is provided. The method includes introducing a biosensor comprising a chimeric polypeptide of the invention in to a cell. The method includes detecting a change in the fluorescent properties of the biosensor in the cell, wherein a change in the fluorescent properties of the polypeptide is indicative of a neoplastic cell. In general a biosensor includes a polypeptide having a membrane translocation specific domain, a first fluorescent domain, a Src homology domain, a phosphorylatable substrate domain and a second fluorescent domain. The method further includes contacting the plasma membrane of the cell with a substrate comprising an agent that binds to a molecule associated with the cytoskeleton of the cell and subjecting the solid or semi solid substrate to a mechanical force sufficient to induce a fluorescence resonance energy transfer (FRET) event in the cell. The method further includes determining the FRET response provided by the biosensor and identifying the cells that provide a response indicative of an absence of plasma membrane wave-propagation.

The term "mechanical force" includes any mechanism for exerting force on a substrate or particle associated with the plasma membrane of a target cell and sufficient to initiate signal transduction across a cell membrane. Accordingly, such a mechanical force is sufficient to initiate "mechanotransduction." A mechanical force can be exerted by, for example, optical forces by contacting a substrate or particle with radiation in the form of a focused beam of light. Generally, the interaction of a focused beam of light with dielectric particles or matter falls into the broad categories of a gradient force and a scattering force. The gradient force tends to pull materials with higher relative dielectric constants toward the areas of highest intensity in the focused beam of light. The scattering force is the result of momentum transfer from the beam of light to the material, and is generally in the same direction as the beam.

In some aspects, a method of the invention includes a radiation source such as infrared laser-tweezers. An "optical tweezer" or "laser tweezer" is a light based system having a highly focused beam to a point in space of sufficiently high intensity that the gradient force tends to pull a dielectric particle toward the point of highest intensity, typically with the gradient force being sufficiently strong to overcome the scattering force. Generally, the laser beam is directed through a microscope objective with a high numerical aperture, with the beam having a diffraction limited spot size of approximately the wavelength of the light, 5,000 to 20,000 angstroms, though more typically 10,000 angstroms. Generally, an optical tweezer has a beam width in the focal plane of 2 um or less, and typically about 1 um.

By utilizing a property of the substrate or particle, such as the optical dielectric constant, the light forces serve to exert a controlled mechanical force on the particle or substrate which may or may not result in detectable displacement of the particle or substrate. The amount and type of force used on the particle need only be sufficient to induce a detectable change in the cytoskeleton of a cell as associated with the plasma membrane. No separation of the particle from any other particle or structure may be required.

In another embodiment, a system for detecting a cell that includes a biosensor of the invention is provided, the system includes a substrate that includes a biological sample having at least one target cell containing a biosensor. In general the cell is associated with a solid or semi solid substrate that includes an agent that binds to a molecule associated with the cytoskeleton of the cell. The system further includes a detector assembly functionally associated with the substrate and configured to capture images associated with a biosensor polypeptide. The system also includes at least one radiation source coupled to the detector assembly and operationally configured to emit radiation sufficient to subject the solid or semi solid substrate to a mechanical force sufficient to induce a fluorescence resonance energy transfer (FRET) event in the cell. The system also includes a controller operably associated with the detector assembly and radiation source. In general the controller is configured to coordinate radiation emission from the radiation source with the image of the target cell captured by the detector assembly.

In some embodiments, a system provided herein further includes a flow path configured to accommodate the target cell in a fluid. In some aspects, the flow path is fluidly connected with a reservoir comprising a plurality of cells. In some aspects, the flow path is a microfluidic flow path.

In some embodiments, the controller is operated by a user and is configured to determine the ratio of fluorescence resonance energy transfer. In some aspects, the controller is further configured to synchronize entry of a cell in to the flow path. As noted above, the radiation source can a laser suitable for imparting a mechanical force on a particle or substrate, such as a bead.

The techniques of this invention may be utilized in a non-guided, i.e., homogeneous, environment, or in a guided environment. A guided environment may optionally include structures such as channels, including microchannels, reservoirs, switches, disposal regions or other vesicles. The surfaces of the systems may be uniform, or may be heterogeneous. Accordingly, structures provided herein can include input channels and output channels. Cells obtained from a biological sample can be stored in a reservoir where they are subjected to transfection with a biosensor of the invention. Subsequently, the cells can be transferred to channels that combine cells contained in a biological sample with particles or substrates (e.g., beads). Subsequent to combining, the mixture can be subjected to an optical force applied to a particular region associated with the structure.

The channels may be formed in a substrate or built upon some support or substrate. Generally, the depth of the channel would be on the order of from substantially 1 to substantially 2 diameters of the particle. For many biological cell sorting or characterization applications, the depth would be on the order of 10 to 20 um. The width of the channels generally would be on the order of from substantially 2 to substantially 8 diameters of the particle, to allow for at least one optical gradient maximum with a width of the order of the particle diameter up to four or more optical gradient maxima with a width of the order of the particle diameter. For many biological cell sorting or characterization applications, the width would be of the order of 20 to 160 micrometers. The channels may have varying shapes, such as a rectangular channel structure with vertical walls, a V-shaped structure with intersecting non-planar walls, a curved structure, such as a semicircular or elliptical shaped channel. The channels, or the substrate or base when the channel was formed within it, may be made of various materials. For example, polymers, such as silicon elastomers (e.g., PDMS), gels (e.g., Agarose gels) and plastics (e.g., TMMA) may be utilized: glass, and silica are other materials. For certain applications, it may be desirable to have the support material be optically transparent. The surfaces may be charged or uncharged. The surface should have properties which are compatible with the materials to be placed in contact therewith. For example, surfaces having biological compatibility should be used for biological arrays or other operations.

Various forms of motive force may be used to cause the particles, substrates and/or cells, typically included within a fluid, to move within the system. Electroosmotic forces may be utilized. As known in the art, various coatings of the walls or channels may be utilized to enhance or suppress the electroosmotic effect. Electrophoresis may be used to transport materials through the system. Pumping systems may be utilized such as where a pressure differential is impressed across the inlet and outlet of the system. Capillary action may be utilized to cause materials to move through the system. Gravity feeding may be utilized. Finally, mechanical systems such as rotors, micropumps, and centrifugation may be utilized.

The systems described herein, and especially a more complex system, may include various additional structures and functionalities. For example, sensors, such as cell sensors, may be located adjacent various channels. Various types of sensors are known to those skilled in the art, including capacitive sensors, optical sensors and electrical sensors. Complex systems may further include various holding vessels or vesicles, being used for source materials or collection materials, or as an intermediate holding reservoir. Complex systems may further include amplification systems. For example, a PCR amplification system may be utilized within the system. Other linear or exponential biological amplification methods known to those skilled in the art may be integrated. Complex systems may further include assays or other detection schemes. Counters may be integrated within the system. For example, a counter may be disposed adjacent an output to tally the number of particles or cells flowing through the output. The systems of the instant invention are useable with microelectromechanical (MEMs) technology. MEMs systems provide for microsized electrical and mechanical devices, such as for actuation of switches, pumps or other electrical or mechanical devices. The system may optionally include various containment structures, such as flow cells or cover slips over microchannels.

A computerized workstation may include a miniaturized sample station with active fluidics, an optical platform containing a laser (e.g., a near infrared laser for biological applications) and necessary system hardware for data analysis and interpretation. The system may include real-time analysis and testing under full computer control.

The inventions herein may be used alone, or with other methods of cell separation. Current methods for cell separation and analysis include flow cytometry, density gradients, antibody panning, magnetic activated cell sorting ("MAC-STM"), microscopy, dielectrophoresis and various physiological and biochemical assays. MACS separations work only with small cell populations and do not achieve the purity of flow cytometry. Flow cytometry, otherwise known as Fluorescent Activated Cell Sorting ("FACSTM") requires labeling.

In yet another aspect, the systems of the present invention may optionally include sample preparation steps and structure for performing them. For example, sample preparation may include a preliminary step of obtaining uniform size, e.g., radius, particles for subsequent optical sorting.

The systems may optionally include disposable components. For example, the channel structures described may be formed in separable, disposable plates. The disposable component would be adapted for use in a larger system that would typically include control electronics, optical components and the control system. The fluidic system may be included in part in the disposable component, as well as in the non-disposable system components.

It will be appreciated by those skilled in the art that there are any number of additional or different components which may be included. For example, additional mirrors or other optical routing components may be used to 'steer' the beam where required. Various optical components for expanding or collimating the beam may be used, as needed.

The methods and apparatus herein permit, a robust cell analysis system suitable for use in high throughput biology in generating pathology reports of tissue, pharmaceutical and life sciences research. This system may be manufactured using higher performance, lower cost optical devices in the system. A fully integrated high throughput biology, cell analysis workstation is suitable for use in drug discovery, drug discovery, toxicology and life science research.

These systems may utilize advanced optical technologies to revolutionize the drug discovery process and cellular characterization, separation and analysis by integrating optophoresis technology in conjunction with a biosensor polypeptide described herein to identify, select and sort specific cells. "Optophoresis" or "Optophoretic" generally relates to the use of photonic or light energy to obtain information about or spatially move or otherwise usefully interact with a particle.

The ability of a cell to perform mechanotransduction of a signal from outside the cell to inside the cell can be reflective of the overall physiologic status of the cell. For example, in a normal cell integrin can be associated with the plasma membrane and the cytoskeleton of the cell. A signal initiated through binding of integrin at the plasma membrane is mechanotransduced to the interior of the cell. Activation of integrin initiates interactions with polypeptides comprising a Src homology domain. Src homology domain containing polypeptides can regulate integrin-cytoskeleton interactions. The impact of this interaction can be detected by a biosensor as described elsewhere in this disclosure. These cellular properties discussed above and throughout this disclosure can be used effectively in drug discovery and pharmaceutical research, since nearly all drugs are targeted ultimately to have direct effects on cells themselves. In other words, drugs designed to effect specific molecular targets will ultimately manifest their effects on cellular properties as they change some aspect of cell physiology which may be detectable through a modification of the cytoskeleton. Therefore, rapid screening of cells for drug activity or toxicity is an application of the technology, and may be referred to as High Throughput Biology.

A computerized workstation may be composed of a miniaturized sample station with active fluidics, an optical platform containing a near infrared laser and necessary system hardware for data analysis and interpretation. The system includes real-time analysis and testing under full computer control. Principal applications of the technology include cell characterization and selection, particularly for identifying and selecting distinct cells from complex backgrounds.

The technology offers a unique and valuable approach to building cellular arrays that could miniaturize current assays, increase throughput and decrease unit costs. Single cell (or small groups of cells) based assays will allow miniaturization, and could allow more detailed study of cell function and their response to drugs and other stimuli. This would permit cellular arrays or cell chips to perform parallel high-throughput processing of single cell assays. It could also permit the standardization of cell chip fabrication, yielding a more efficient method for creation of cell chips applicable to a variety of different cells types.

The cytoskeleton is a complex of structural proteins which keeps the internal structure of the cell intact. Many drugs such as taxol, vincristine, etc. . . . as well as other external stimuli such as temperature are known to cause the cytoskeleton to be disrupted and breakdown. Optophoresis provides a means to monitor populations of cells for perturbations in the cytoskeleton. Accordingly, methods and systems provided herein can be used to detect neoplastic cells in a pathology sample. Methods and systems provided herein can be used to identify cells which are undergoing programmed cell death or apoptosis in the context of identifying specific drugs or other phenomenon which lead to this event. The present methods can be used to identify which cells are undergoing apoptosis and this knowledge can be used to screen novel molecules or cell conditions or interactions which promote apoptosis. Any phenomena which can modify polypeptides associated with the cytoskeleton of a cell can be detected by the present methods. These phenomena include biological events such as viral infection. In addition, cells with bound ligands, peptides, growth factors can be detected. Many compounds and proteins bind to receptors on the surface of specific cell types. Such ligands may then cause changes inside the cell. Many drug screens look for such interactions. Optophoresis provides a means to monitor binding of exogenous large and small molecules to the outside of the cell, as well as measurement of physiological changes inside the cell as a result of compound binding.

In another example, a panel of 60 tumor cell lines has been established by the National Cancer Institute as a screening tool to determine compounds which may have properties favorable to use as chemotherapeutic agents. It should be possible to use methods and systems provided herein to array all 60 lines and then to challenge them with known and novel chemicals and to monitor the cell lines for response to the chemicals.

The interactions of microspheres with cells or other compounds has been used in a number of in vitro diagnostic applications. Compounds may be attached to beads and the interactions of the beads with cells or with beads with other compounds on them can be monitored by optophoresis.

It is understood that detector assembly can be adapted to include any mechanism suitable for detecting an image generated by a system provided herein. In exemplary embodiments discussed above, the detector assembly is a CMOS (complementary metal oxide semiconductor) imager. As used herein, CMOS refers to both a particular style of digital circuitry design, and the family of processes used to implement that circuitry on integrated circuits. Accordingly, a CMOS imager may include a chip with a large number of CMOS transistors packed tightly together (i.e., a "Complementary High-density metal-oxide-semiconductor" or "CHMOS"). Alternatively, or additionally, a CMOS imager may include a combination of MEMS sensors with digital signal processing on one single CMOS chip (i.e., a "CMOSens"). Additional detectors include, for example, an array of charge coupled devices ("CCDs"), a camera with photosensitive film, or a Vidicon camera.

Controller optionally includes a storage device for storing images detected by detector assembly. Controller can further optionally include algorithm(s) for analyzing the images stored by storage device, and provides a user with information about status of a cell (e.g., normal or neoplastic) based on the analysis. General methodology for data acquisition and reduction to measure FRET and FRET-ratios are known to those skilled in the art.

In any of the embodiments described above, controller can be a computer that includes hardware, software, or a combination of both to control the other components of the system and to analyze the phase-shifted images to extract the desired information about the test object. The analysis described above can be implemented in computer programs using standard programming techniques. Such programs are designed to execute on programmable computers each comprising a processor, a data storage system (including memory and/or storage elements), at least one input device, at least one output device, such as a display or printer. The program code is applied to input data (e.g., images from a CMOS imager) to perform the functions described herein and generate information which is applied to one or more output devices. Each computer program can be implemented in a high-level procedural or object-oriented programming language, or an assembly or machine language. Each such computer program can be stored on a computer readable storage medium (e.g., CD ROM or magnetic diskette) that when read by a computer can cause the processor in the computer to perform the analysis described herein.

EXAMPLE 1

There are several disadvantages to deliver genes into cells with transient transfection for cancer detection. First, the efficiency is low and therefore may result in the failure of the identification of cancerous cells that are not transfected. Second, the transfection method requires at least 24 hr to complete the process, which may complicate the maintenance of tissue samples and, most importantly, affect the cellular functions of tissue samples and therefore decrease the accuracy of the signals detected by the biosensor. Finally, the protein expression levels vary among transfected cells. In contrast, a protein-based Tat-fused Src biosensor can be introduced into cells with 100% efficiency within minutes. The protein expression levels among different cells can be well controlled. This will allow an accurate and rapid cancer diagnostic screening of biopsy samples.

Fusion of a Tat peptide at the N-terminal of CFP: The gene encoding the CFP may be PCR amplified by using a sense primer containing the gene sequence of the Tat peptide and a BamHI site, and a reverse primer containing a SphI site. Pfu DNA polymerase may be employed to ensure high fidelity in the PCR reaction.

The PCR product and the bacterial expression plasmid (PRSETb) containing a previous version of Src biosensor may be digested with BamHI and SphI. The digested vector and insert may be ligated with T4 ligase and sequenced to verify the accuracy of cloning.

The bacterial expression plasmid containing the Tat-fused Src biosensor may be transformed into *E. coli*. The expressed biosensor proteins may be harvested and purified using His-tag column purification system. The concentration of the purified proteins may be measured using an absorbance photospectrometer before being aliquoted and stored in −80° C.

The Tat-fused biosensor proteins may be incubated with different cell lines for various durations. The cells may then be examined by fluorescence microscopy to determine their cellular fluorescence intensity. The cells may be subsequently washed and lysed. The cellular biosensor protein levels may be determined by immunoblotting with anti-GFP antibodies to confirm the delivery efficiency. Quantitative charts of fluorescence intensities vs. cell lines or incubation time may be generated to provide a guide for optimal introduction of the Tat-fused Src biosensor into different cell lines.

The Tat-fused bacterial expression plasmid may provide a convenient and high-yield protein production system. The protein delivery efficiency in different cell lines is expected to be 100%. Alternative amino acids sequence of the Tat peptide, including the length and order, may be tested to generate a high-efficiency and fast-delivery Tat peptide.

The Tat-fused proteins pass across the plasma membrane through macropinocytosis and some of them can be retained in macropinosomes. To release the Tat-fused proteins into the cytoplasm and become functional, a Tat-fused HA2 peptide may be incubated together with the Tat-fused biosensor proteins during the protein delivery process. This HA2 peptide can disrupt the lipid membrane of macropinosomes and release the Tat-fused biosensor proteins into the cytoplasm.

Therefore, this protein-based TAT-HA2 method should have a high delivery efficiency of functional biosensor proteins into the cells.

For each selected cell type, varying amounts of Tat-fused HA2 peptides may be applied on cells together with the Tat-fused biosensor proteins. The uptake efficiency of the biosensor proteins may be examined as described above.

For each selected cell type, varying amounts of Tat-fused HA2 peptides may be applied on cells together with the Tat-fused biosensor proteins. The treated cells may be fixed and stained with the specific marker FM4-64 to label macropinosomes. The ratio of the overall CFP fluorescence intensities within and outside of the macropinosomes, which may be highlighted by FM4-64 with red color, may be used as the criterion to represent the efficiency of HA2 peptide in releasing biosensors into the cytoplasm. The results of such titration experiments may allow us to determine the amount of the peptide that yields maximal efficiency.

The TAT-HA2 method as described above may be employed to introduce the Tat-fused biosensor proteins into cells. The treated HaLa cells may be subjected to fluorescence microscopy and observed for the FRET ratio change upon stimulation with 50 ng/ml EGF. The FRET responses may be compared to the cells micro-injected with the same amount of Tat-fused biosensor proteins to assess the delivery efficiency of functional biosensors.

In alternative embodiments, HA2 may be fused in the same molecule at the C-terminal of the Tat-fused biosensor so that the two distinct functional domains (biosensor and HA2) may share the same Tat sequence and the same macropinosomes to avoid interfering with each other.

It has been shown that Src activity is regulated differentially in normal and cancer cells, and is closely correlated to the malignant potential of the cancer cells (3; 6). Therefore, monitoring Src activity in biopsy samples with the protein-based TAT-HA2 method will provide a practical standard for identifying cancerous cells, even at a very low percentage, among normal cells and assessing the early cancer development.

Biopsy tissue samples may be incubated with various amounts of Tat-fused HA2 and biosensors for different durations. The samples may be examined by fluorescence microscopy to determine the percentage of cells carrying the desired fluorescence proteins and the fluorescence intensity of these cells. These titration experiments will allow us to determine the optimal amounts of Tat-fused HA2 and biosensors and the duration that yield the maximal efficiency.

It has been shown that the Tat-mediated protein delivery process is independent of temperature or energy. Various amounts of Tat-fused HA2 and biosensors may be incubated with tissue samples at different temperatures for different durations. The samples may be examined by the procedures described in specific embodiments described above to assess the effects of temperature on protein delivery efficiency.

The Tat-fused HA2 and biosensors may be incubated with tissue samples, which may be subsequently subjected to EGF stimulation. Time-lapse fluorescence intensity images may be collected by an inverted fluorescence microscope, and CFP/YFP emission ratio images may be computed by Metaflour software. These FRET responses may be compared to the cells micro-injected with same amount of Tat-fused biosensor proteins to assess the delivery efficiency of functional biosensors into biopsy samples.

EXAMPLE 2

HeLa cells transfected with the Src reporter, epidermal growth factor (EGF) induced a 25-35% emission ratio change (FIG. 5, panel A). Introduction of the reporter did not affect the ERK activity with or without EGF stimulation, suggesting that the reporter need not perturb endogenous cellular signaling. Mutations of either or both of the putative Src phosphorylation sites (Tyr 662 and 664) to Phe in the substrate peptide (FIG. 4, panel A) prevented the FRET response to EGF in HeLa cells (FIG. 5, panel B). Mutation of Arg 175 to Val (FIG. 4, panel A), eliminating SH2 domain binding to phosphorylated peptides 15, also abrogated the EGF-induced FRET response. These results validate the phosphorylation-induced intramolecular (intra-reporter) interaction between the SH2 domain and substrate peptide as the mechanism for the FRET response. Immunoblotting revealed that EGF-induced tyrosine phosphorylation is abolished only by mutating both Tyr 662 and 664, but not either site alone (FIG. 5, panel C), unlike the blockade of the FRET response by single mutations (FIG. 5, panel B). Thus, the SH2 binding requires not only the phosphorylation of one of the two Tyr residues but also the integrity of the other Tyr in the substrate, consistent with the notion that the neighboring amino acids of the phosphorylated site are important for SH2 binding 16. Disruption of the SH2 domain by R175V mutation also blocked the EGF-induced tyrosine phosphorylation of the Src reporter (FIG. 5, panel C), suggesting that the SH2 domain of the reporter may assist in its association with activated Src to facilitate the phosphorylation process.

The EGF-induced FRET response in HeLa cells was reversed by PP1, a selective inhibitor of Src family tyrosine kinases, and was markedly reduced after pretreatment with PP1 (FIG. 5, panel D). The normal platelet-derived growth factor (PDGF)-induced FRET response of the Src reporter was abolished in Src/Yes/Fyn triple knockout (SYF2/2) mouse embryonic fibroblasts (MEF) (FIG. 5, panel E). Reconstitution of these SYF2/2 cells with c-Src, but not c-Fyn, restored the FRET response. Reconstitution with c-Yes caused only a weak FRET response of the Src reporter. The small and delayed FRET response observed in the kinase-dead c-Src (Src_KD) group may be attributed to the residual activity of Src_KD. These results demonstrated the specificity of the Src reporter toward Src in mammalian cells.

CFP and FYP can form anti-parallel dimers 17. To eliminate the unintended FRET resulting from intermolecular (between reporters) dimerization, we introduced A206K mutations into CFP and YFP to generate monomeric CFP and YFP18 (FIG. 4, panel A). These mutations did not alter the spectral properties of the Src reporter, but they led to a better dynamic range of FRET (43 versus 25% emission ratio change) in response to Src kinase in vitro (compare FIG. 5, panel F with FIG. 4, panel C) and a greater EGF-induced FRET response in HeLa cells that was reversible by EGF washout (FIG. 5, panel G and FIG. 8). This monomeric reporter was used for the study of mechano-activation of Src.

Figure 9:
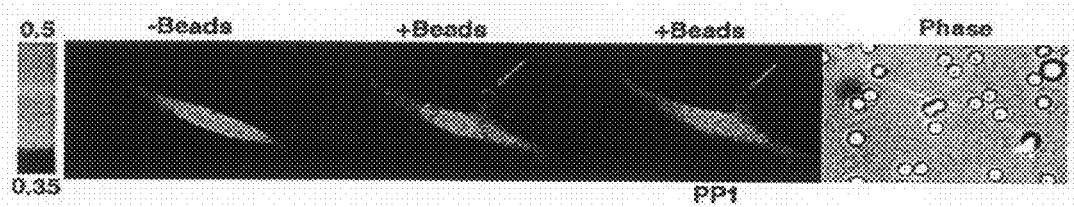
FIG. 9 provides images indicating that the FRET response induced by the Fibronectin-coated beads is specific to Src. HUVECs expressing the Src reporter were incubated with fibronectin-coated beads, followed by the addition of PP1 (10 uM). Arrows point to the cell area around a bead before and after the PP1 application. The phase contrast image on the right shows the positions of the beads and cell body.
Figure 10:
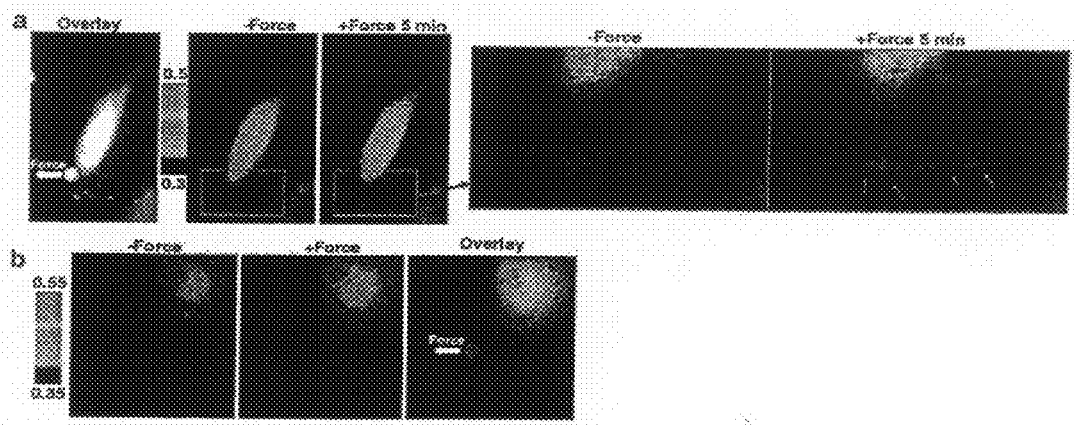
FIG. 10, panel A provides images indicating that mechanical forces induced FRET responses of the cytosolic Src reporter when imposed on fibronectin-, but not polylysine-coated beads. Fibronectin-coated beads were incubated for 20 min with HUVECs expressing the Src reporter, as indicated by the image on the far left. Laser-tweezers were used to apply a steady 300-pN mechanical force (towards the left) on the bead. The two CFP/YFP emission ratio images of the cell correspond to before and 5 min after force application. Enlarged images of the boxed area are shown on the right.

Beads coated with fibronectin, which binds to integrins and hence causes coupling with the cytoskeleton 19, were applied to HUVECs. Consistent with the observation of Src activation by integrin clustering 7, the fibronectin-coated beads caused a local FRET response of the Src reporter around the beads (FIG. 6, panel A), reversible by PP1 (FIG. 9). Single-beam gradient optical laser-tweezers with controlled mechanical force (300 pN) were used to pull the adhered beads. FRET responses occurred in focal complex-like regions at the cell periphery without detectable bead displacement (FIG. 10, panel A). Polylysine-coated beads subjected to the same mechanical force did not induce any significant FRET response (FIG. 10, panel B), suggesting that specific integrin-cytoskeleton coupling is needed for the mechanotransduction.

Figure 11:
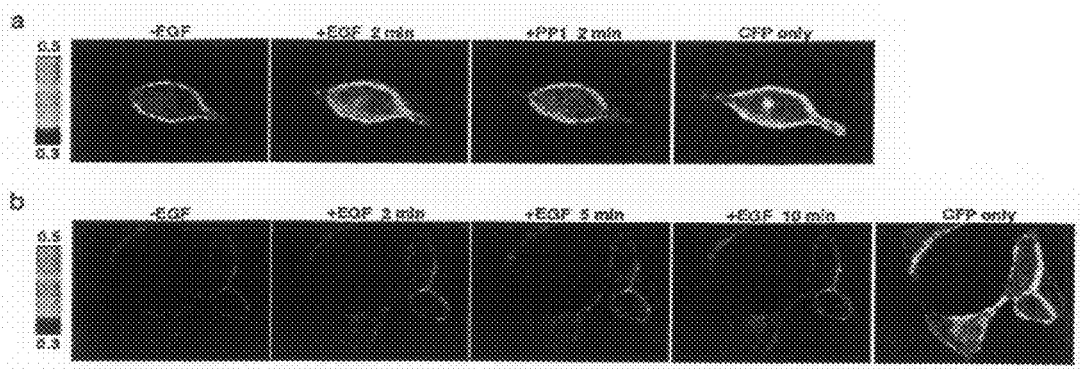
FIG. 11, panel A provides images indicating that EGF-induced FRET responses of the membrane-targeted Src reporter are specific to Src. HeLa cells expressing the membrane-targeted Src reporter were stimulated with EGF (50 ng/ml), followed by the application of PP1 (10 uM). The representative emission ratio images are shown on the left and the CFP-only image is shown on the far right.

The thin lamellipodia at the cell periphery, which are important in mechanotransduction, contain only limited copies of cytosolic Src reporters. Because significant amounts of CFP/YFP molecules are required to yield enough fluorescence above the endogenous autofluorescence background 20, there is a need for controlled localization of the Src reporter to enhance its effective local concentration, especially in lamellipodia. Because the translocation of Src to the plasma membrane is a prerequisite for Src activation 7,21, we targeted the monomeric Src reporter to the plasma membrane with a fusion of the 16 N-terminal residues from Lyn kinase 18. The EGF-induced FRET response of this membrane-targeted reporter was reversed by PP1 (FIG. 11, panel A) and prevented by pretreatment with PP1 (FIG. 11, panel B), indicating its specificity towards Src (FIG. 6, panel B).

Figure 12:
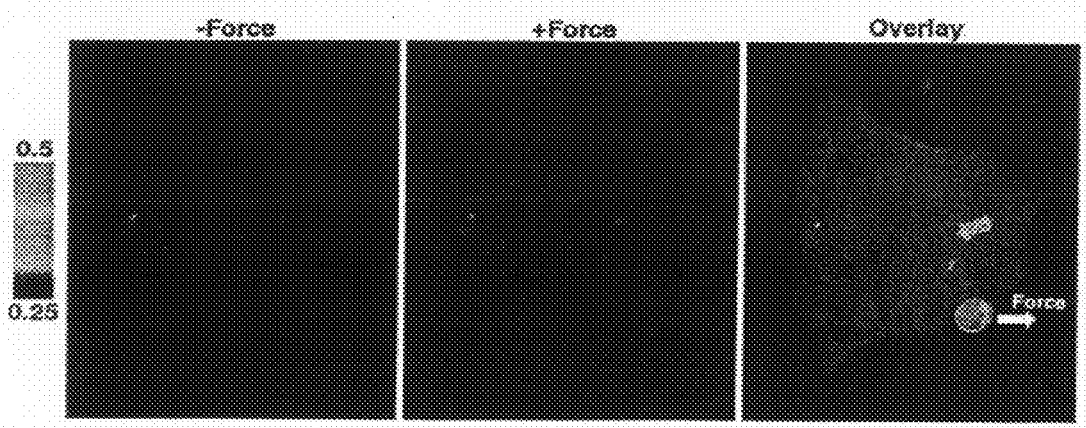
FIG. 12 provides images indicating that mechanical forces imposed on polylysine-coated beads did not induce the FRET responses of the membrane-targeted Src reporter. Polylysine-coated beads were incubated with HUVECs for 20 min, as indicated by the image on the far right. Laser-tweezers were used to apply a steady 300-pN mechanical force (towards the right) on the bead. The two CFP/YFP emission ratio images of the cell correspond to before and 15 min after force application.
Figure 13:
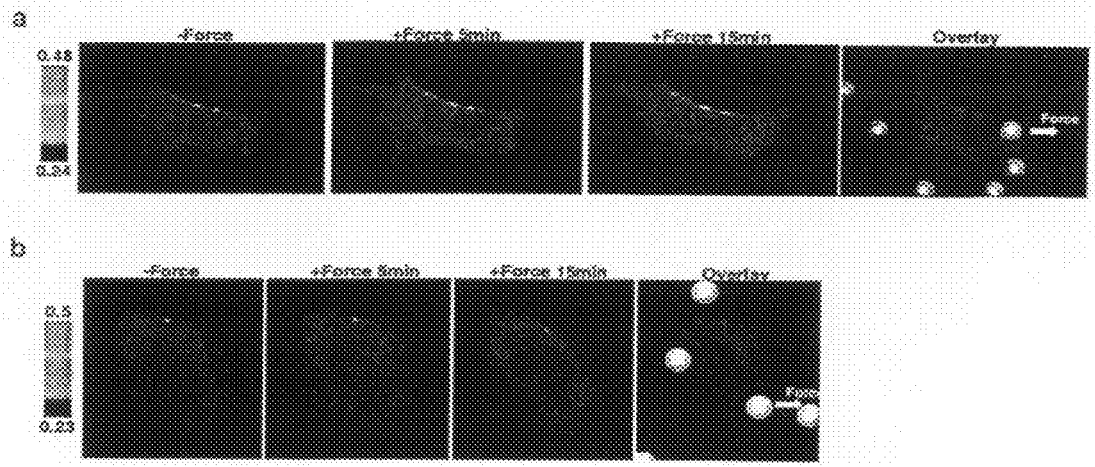
FIG. 13, panel A provides images indicating that mechanical forces on fibronectin-coated beads did not induce FRET responses of inactive mutant Y662F/Y664F of the membrane-targeted Src reporter. Fibronectin-coated beads were incubated with HUVECs expressing the mutant Y662F/Y664F of the membrane-targeted Src reporter, as indicated by the images on the far right. Laser-tweezers were used to apply a steady 300-pN mechanical force (towards the right) on the bead. The time-lapse CFP/YFP emission ratio images of the cells correspond to before and after force application are shown on the left as indicated.

The application of pulling force via the laser tweezers on a bead coated with fibronectin, but not polylysine (FIG. 12), on the HUVECs expressing the membrane-targeted Src reporter led to a directional FRET response, with the majority of activations transmitted towards distal areas of the cell opposite to the force direction (FIG. 6, panel C). This transmission consisted of an immediate distal Src activation and a slower wave-propagation of Src activation followed by lamellipodia protrusions at the cell periphery (FIG. 6, panel C). Such FRET responses were absent with inactive reporters (for Y662F/Y664F see FIG. 13, panel A; for R175V see FIG. 13, panel B). In experiments where the speed of the wave propagation of Src-activation away from the stimulation site can be clearly measured, it was found to be $18.1\hat{ }1.7$ nm s21 (mean$\hat{ }$s.e.m.) (FIG. 6, panel D). This result indicates that a local force caused a directional and long-range transduction of Src-activation wave to spatial destinations.

Figure 14:
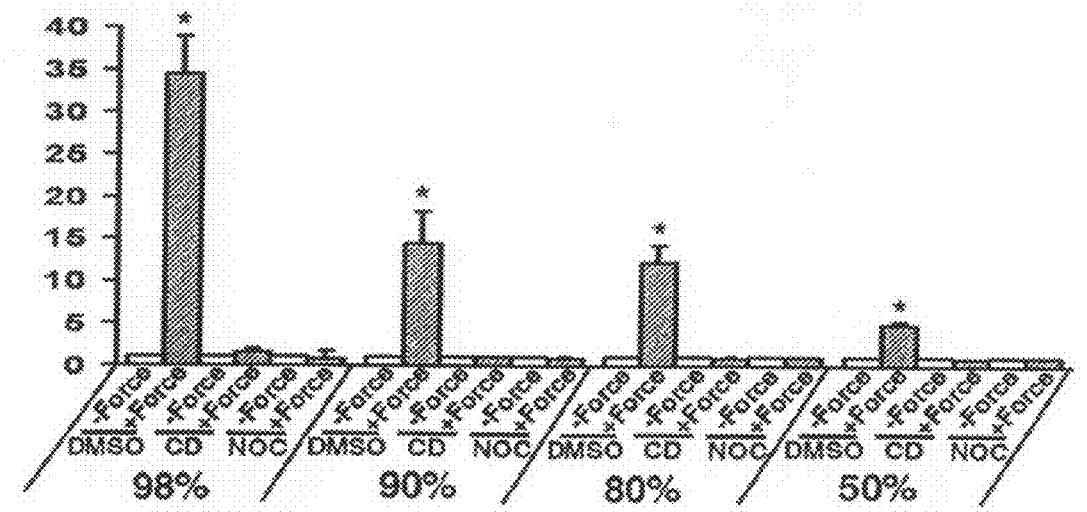
FIG. 14 is a bar graph depicting the results of HUVECs treated with cytochalasin D, Nocodazole, or DMSO and subjected to mechanical-force for 15 min or kept as static control. The numbers of distally-activated pixels were calculated with a cut-off intensity threshold of 98%, 90%, 80%, or 50%. Bar graphs represent mean±SD of the force-induced fold induction of distally-activated pixel numbers. The asterisks indicate significant differences (p<0.05) between the samples subjected to mechanical force and their corresponding controls.

The roles of the cytoskeleton on this force-induced Src activation was determined. Disruption of actin filaments with cytochalasin D or microtubules with nocodazole blocked the force-induced distal, but not local, FRET responses (FIG. 7, panel A and panel B). Polarity analysis of Src activation, by averaging the emission ratios of 36 evenly divided angular sections of each cell with the bead position as the centre, revealed that the local pulling force caused a cytoskeleton-dependent polarized FRET response pointing to the opposite direction (FIG. 7, panel D and panel D). Statistical analysis further showed that the mechanical force caused a cytoskeleton-dependent increase of the number of pixels with highly activated Src distal to the force-imposed bead, indicating a long-range mechano-activation of Src (FIG. 7, panel E and FIG. 14).

It is unclear where mechano-induced biochemical signals are initiated and how they are transmitted in the cell. Green fluorescent protein (GFP)-tagged fluorescent markers have been used to study the displacement of cellular organelles and the formation of a focal adhesion complex induced by mechanical stimuli, but these inert fluorescence markers cannot monitor the dynamic signal transduction process. Our FRET-based Src reporter enables the visualization and quantification of the mechano-activated Src with high temporal and spatial resolution in live cells. The results indicate that local mechanical stimulation triggers a directional and long-range propagation of Src activation, for which cytoskeleton integrity is essential.

Integrin-mediated activation of Src at local sites by mechanical stimuli may induce p130cas/Dock180 association, Rac-Arp2/3 activation, cortical actin network nucleation and polymerization, and actin-ruffle extensions. These Rac and actin activities in turn promote the recruitment and activation of Src at the tip of these newly assembled wave-like actin ruffles, thus further inducing the in situ Rac activation and actin polymerization. This positively coordinated mechanism may result in a wave propagation of Src activation. The directionality of this wave propagation may be attributed to the initial local mechanical tension generated in a direction counter to the applied force. The applied force can also be mechanically transmitted quickly through tensed cytoskeleton network to distal locations and to activate Src. This directional Src activation may release the tension at desired destinations and rearrange the intracellular stress distribution, thus serving as a feedback mechanism for the cell to adapt to new mechanical environments (FIG. 7, panel F).

A 1064-nm continuous-wave diode-pumped ND:YVO4 laser with 5 W power (Spectra-Physics) was used for the laser tweezers experiments. The laser beam passes through a laser-beam expander, a steering mirror, and a dichroic long-pass beamsplitter to enter the microscope side port.

The gene for the Src reporter was constructed by polymerase chain reaction (PCR) amplification of the complementary DNA from the c-Src SH2 domain with a sense primer containing a SphI site and a reverse primer containing the gene sequence for a flexible linker, a substrate peptide derived from p130cas, and a SacI site. The PCR products were fused together with an N-terminal enhanced CFP and a C-terminal citrine (a version of enhanced YFP) 10, as shown in FIG. 4, panel A. Mutations of Y662/664F, Y662F, Y664F, R175V and A206K were conducted with the QuickChange method (Stratagene) Constructs were cloned into pRSETB (Invitrogen) using BamHI/EcoRI for bacterial expression and into pcDNA3 (Invitrogen) behind a Kozak sequence using HindIII/EcoRI for mammalian cell expression. The membrane-targeted CFP was constructed by PCR amplification of the monomeric CFP with a sense primer containing the codes for 16 N-terminal amino acids from Lyn kinase 18 to produce a membrane-targeted Src reporter.

The various Src reporters and their mutants used in FIG. 5, panels B and C are abbreviated as: WT, the Src reporter (wild type);DM, Y662F and Y664F double mutations in the designed substrate peptide; Y662F or Y664F, the Y662F or Y644F single mutation in the substrate peptide, respectively; and R175V, the R175V mutation in the binding pocket of the SH2 domain.

The various mouse embryonic fibroblasts (MEFs) and knockout cell lines used for specificity studies in FIG. 5, panel E are: wild type (control), Src/Yes/Fyn triple-knockout (SYF), SYF reconstituted with c-Src (SYF+Src), c-Fyn (SYF+Fyn), c-Yes (SYF+Yes), or K295R kinase-dead c-Src (SYF+Src_KD).

The HeLa or MEF cells expressing the desired exogenous proteins were starved with 0.5% FBS for 36-48 h before being subjected to EGF (50 ng ml$^{-1}$) or PDGF (10 ng ml$^{-1}$) stimulation. During imaging, the cells were maintained in Hanks' balanced salt solution (HBSS) with 20 mMHEPES (pH 7.4) and 2 g l$^{-1}$ D-glucose at 25° C. Images were collected by using MetaFluor 6.0 software (Universal Imaging) with a 440DF20 excitation filter, a 455DRLP dichroic mirror, and two emission filters controlled by a filter changer (480DF30 for CFP and 535DF25 for YFP).

To image the mechanical-force-induced Src activation, HUVECs were first starved with 0.5% FBS for 24 h and then kept in $CO_2$-independent medium without serum (Gibco BRL) at 37° C. in a thermostatic chamber. A Zeiss axiovert inverted microscope equipped with a 440DF20 excitation filter and a 455DRLP dichroic mirror was integrated with the laser-tweezers. CFP and YFP emission images were acquired simultaneously with an ORCA ER CCD camera (Hamamatsu) through a Dual-View module (Optical-Insights). The CFP and YFP images were aligned pixel-by-pixel with our customized Matlab program by maximizing the normalized cross correlation coefficient of CFP and YFP fluorescence intensity images:

$$\text{corr} = \frac{\sum_i \sum_j (C_{ij} - \overline{C})(Y_{ij} - \overline{Y})}{\sqrt{\left(\sum_i \sum_j (C_{i,j} - \overline{C})^2\right)\left(\sum_i \sum_j (Y_{ij} - \overline{Y})^2\right)}}$$

where $C_{i,j}$ and $Y_{i,j}$ are the intensity values at pixels (i, j) of the CFP and YFP images, and C and Y are the mean intensity values of the CFP and YFP images. The ratio images of aligned CFP/YFP were computed and created by the MetaFluor software to represent the FRET efficiency.

By taking the derivative of rho 2/B(κ) in Otsu's method and calculating its first local minimum, a non parametric method was developed to calculate the intensity threshold to differentiate the edges of HUVECs from the background in CFP or YFP fluorescence intensity images. The intensity threshold was used to generate a binary mask image with values outside the cell set at zero to select the pixels located within the cell body in the CFP/YFP emission ratio images. For polarity analysis, a customized Matlab program was used to evenly divide a HUVEC into 36 angular sections with the bead position as the centre and the force direction as the zero degree axes for v, as illustrated in FIG. 7, panel C. For statistical analysis of long-range activation of Src, a pixel located within a cell at a given time is defined as 'distally activated' when: (1) its emission ratio value is above a certain percentage (98%, 90%, 80% and 50% were used as the thresholds) of pixel population in the same cell after 15 min of force stimulation, and (2) the distance between the pixel and the centre of the force-imposed bead is larger than half of the virtual radius of the cell, as shown in the following formula:

$$\sqrt{(x - x_0)^2 + (y - y_0)^2} > \frac{R}{2} = \frac{1}{2}\sqrt{\frac{A}{\pi}}$$

where x, y are the coordinates of any given pixel within the cell body, $x_0$, $y_0$ are the coordinates of the force-imposed bead centre, R is the virtual radius for the cell, and A is the area of the cell.

To generate retrovirus expression plasmids, the various Src reporters were inserted into the HindIII/XhoI restriction sites of the PCLNCX retrovirus expression vector (Imgenex).

Chimeric proteins were expressed as N-terminal 6×His tag fusions in *Escherichia coli* and purified by nickel chelation chromatography. Fluorescence emission spectra of the purified reporters were measured in a cuvette with an excitation wavelength of 434 nm. Emission ratios of CFP/YFP (476 nm/526 nm) were measured before and after adding ATP (1 mM) into the kinase assay buffer at 25° C. that contained a mixture of various reporters and kinases as indicated.

Cell culture reagents were obtained from GIBCO BRL. The culture medium for HeLa, MEF, SYF−/−, and 293 cells was Dulbecco's modified Eagle's medium (DMEM) supplemented with 10% fetal bovine serum, 2 mM L-glutamine, 1 unit/ml penicillin, 100 ug/ml streptomycin, and 1 mM sodium pyruvate. HUVECs were maintained in endothelium growth medium (EGM; Cambrex). The different kinds of cells were cultured in a humidified 95% air, 5% $CO_2$ incubator at 37° C. before experiments.

The various plasmids were transfected into HeLa, MEF, SYF−/−, or 293 cells at 80% confluence using the lipofectamine method (Invitrogen). The RetroMax retroviral expression system (Imgenex) was used to introduce genes into HUVECs. Various Src reporters incorporated in PCLNCX vector were co-transfected with PCL-Ampho packaging vector into 293 cells by using lipofectamine. The supernatant of about 293 cells was collected after 2 days of transfection and filtered through 0.45 um pore filters. HUVECs were infected with 1:1 mixture of the collected supernatant and fresh EGM in the presence of 8 ug/ml polybrene.

Actin filaments or microtubules were disrupted by incubation with cytochalasin D (0.2 uM; from Sigma) or Nocodazole (1 uM; from Sigma), respectively, for 1 hr. A rabbit polyclonal anti-GFP antibody (ab290; from Abcam) was used for immunoprecipitation (IP) and a mouse monoclonal anti-GFP antibody (BD Biosciences) was used for immunoblotting (IB). A mouse monoclonal anti-phospho-tyrosine (clone 4G10; Upstate) was used for IB to detect the phospho-tyrosine level of proteins.

The HeLa cells expressing the various Src reporters, with or without mutations, had been starved with 0.5% FBS for 36-48 hr before they were subjected to EGF (50 ng/ml) stimulation or kept as control. Cell lysates from the various samples were subjected to IP with an anti-GFP antibody to pull down the expressed reporters, followed by IB with an anti-phospho-tyrosine antibody (Anti-pY) to display the tyrosine phosphorylation level, or an anti-GFP antibody to show the expressed protein level. The molecular weight of the Src reporter is about 70 KD.

The laser trapping force was calibrated using the viscous drag method in which the microscope stage velocity and therefore viscous force was gradually increased until the viscous drag on a trapped 10-um bead was just sufficient to pull it out of the trap. This critical force is a measure of the maximum trapping force, at a given laser power, exerted on the bead. For the 470 mW of laser power used in our experiments, the maximum laser-trapping force was found to be 450 pN. Since the maximum trapping force occurs when the laser focus is away from the center and close to the edge of the bead, the experimental trapping force with the laser focused at 3.7 um off the bead center in our experiments was calculated from the Ashkin model of trapping force to be 300 pN. Polystyrene beads (10 um; from Polysciences Inc) were coated with fibronectin (50 ug/ml) or polylysine (100 ug/ml). After the incubation of the coated beads with HUVECs for 20 min, beads seeded on cells were selected and subjected to directional steady mechanical forces exerted by laser-tweezers.

ECs may be fixed with 4% paraformaldehyde in PBS for 20 min at room temperature, permeabilized with 0.5% Triton X-100 for 10 min and blocked with 5% normal goat serum in PBS for 1 hr. The cells may then be incubated with various primary antibodies as indicated, washed with PBS, and labeled with the fluorescence-conjugated secondary antibodies for microscopic examination.

A Zeiss Axiovert inverted fluorescence microscope with a cooled charge-coupled device camera (Photometrics), a filter changer (Lambda 10-2, Sutter Instruments), a 440DF20 excitation filter, a 455DRLP dichroic mirror, and two emission filters (480DF30 for ECFP and 535DF25 for citrine) may be used. The system may be controlled and the pixel-wise cyan/yellow ratio images may be generated by METAFLUOR software (Universal Imaging).

Different kinds of cells may be cultured in DMEM containing 10% fetal bovine serum and maintained in a humidified 5% $CO_2$-95% air incubator at 37° C. The cells can be lysed in a buffer containing 25 mM Tris-HCl, pH 7.5, 150 mM NaCl, 1% Triton-X-100, 0.1% SDS, 5 mM NaF, 1 mM Na3VO4, 1 mM PMSF, and 10 ug/ml Leupeptin. Proteins separated on the SDS-PAGE may be transferred to a nitrocellulose membrane. The membrane may then be blocked with 5% bovine serum albumin, followed by incubation with the primary antibody. The bound primary antibodies may be detected by using a goat anti-rabbit IgG-horseradish peroxidase conjugate (Santa Cruz Biotechnology) and the ECL detection system (Amersham Pharmacia Biotech).

A number of embodiments of the invention have been described. Nevertheless, it will be understood that various modifications may be made without departing from the spirit and scope of the invention. Accordingly, other embodiments are within the scope of the following claims.

What is claimed is:

1. A chimeric polypeptide comprising, in operative linkage, a lipid membrane destabilization domain, a membrane translocation specific domain selected from the group consisting of a *drosphila* homeoprotein antennapedia transcription polypeptide, a herpes simplex virus structural protein VP22 polypeptide and a HIV-1 transcription activator Tat polypeptide; a first fluorescent domain; a Src homology domain (SH2); a phosphorylatable Src substrate domain comprising the amino acid sequence WMEDYDYVHLQG (SEQ ID NO:2); and a second fluorescent domain, wherein the first and the second fluorescent domains are different.

2. The polypeptide of claim 1, wherein the lipid destabilization domain comprises hemagglutinin protein (HA2).

3. The polypeptide of claim 1, wherein the first and second fluorescent domains are selected from the group consisting of green fluorescent proteins (GFPs), red fluorescent proteins (RFPs), cyan fluorescent protein (CFP), monomeric GFP (mGFP), a monomeric CFP (mCFP), yellow fluorescent protein (YFP), monomeric YFP (mYFP), or a spectral variant thereof.

4. The polypeptide of claim 1, wherein the first and the second fluorescent domains exhibit a detectable resonance energy transfer when the first fluorescent domain is excited.

5. The polypeptide of claim 1, comprising, in an orientation from the amino terminus to carboxy terminus, a lipid membrane destabilization domain, a membrane translocation specific domain, a first fluorescent domain, a Src homology domain, a phosphorylatable Src substrate domain, and a second fluorescent domain.

6. The polypeptide of claim 1, wherein at least one amino acid of the phosphorylatable Src substrate domain is phosphorylated.

7. The polypeptide of claim 1, further comprising a polypeptide linker domain.

8. The polypeptide of claim 1, wherein the membrane translocation specific domain comprises the amino acid sequence RRRQRRKKRG (SEQ ID NO:1).

9. An isolated host cell containing the polypeptide of claim 1.

10. An isolated polynucleotide encoding the polypeptide of claim 1.

11. The polynucleotide of claim 10, which is operatively linked to an expression control sequence.

12. An isolated vector comprising the polynucleotide of claim 10.

13. The vector of claim 12, which is an expression vector.

14. The vector of claim 13, wherein the expression vector is a bacterial cell, insect cell, or mammalian cell expression vector.

15. An isolated host cell containing the polynucleotide of claim 10.

16. A kit comprising the polynucleotide of claim 10.

17. A kit comprising the vector of claim 14.

18. A kit comprising the polypeptide of claim 1.

19. A method for measuring Src activation, the method comprising: a) transfecting a cell with the polypeptide of claim 1; and b) detecting a change in fluorescent properties of the polypeptide in the cell; wherein a change in the fluorescent properties of the polypeptide is indicative of Src activation.

* * * * *